(12) United States Patent
Kimura

(10) Patent No.: US 12,249,071 B2
(45) Date of Patent: Mar. 11, 2025

(54) IMAGE PROCESSING SYSTEM, ENDOSCOPE SYSTEM, AND IMAGE PROCESSING METHOD

(71) Applicant: OLYMPUS CORPORATION, Tokyo (JP)

(72) Inventor: Masato Kimura, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 475 days.

(21) Appl. No.: 17/886,698

(22) Filed: Aug. 12, 2022

(65) Prior Publication Data

US 2022/0392069 A1 Dec. 8, 2022

Related U.S. Application Data

(63) Continuation of application No. PCT/JP2020/006965, filed on Feb. 21, 2020.

(51) Int. Cl.
*G16H 50/20* (2018.01)
*A61B 1/00* (2006.01)
(Continued)

(52) U.S. Cl.
CPC ........ *G06T 7/0012* (2013.01); *A61B 1/00009* (2013.01); *A61B 5/02042* (2013.01);
(Continued)

(58) Field of Classification Search
CPC ......... G06T 7/0012; G06T 2207/10016; G06T 2207/10068; G06T 2207/20081;
(Continued)

(56) References Cited

U.S. PATENT DOCUMENTS 11,206,984 B1 * 12/2021 Boveja ................. A61B 5/0082
11,625,825 B2 * 4/2023 Cantrall ............... A61B 5/7225
600/117

(Continued)

FOREIGN PATENT DOCUMENTS

| JP | 2011036371 A | 2/2011 |
| JP | 2018114303 A | 7/2018 |
| WO | 2019181432 A1 | 9/2019 |

OTHER PUBLICATIONS

International Search Report dated May 19, 2020 issued in PCT/JP2020/006965.

*Primary Examiner* — Cindy Trandai

(74) *Attorney, Agent, or Firm* — Scully, Scott, Murphy & Presser, P.C.

(57) ABSTRACT

An image processing system includes at least one processor including hardware. The processor performs a process that acquires, as a processing target image sequence, images captured in a time series manner with an inside of a living body by an endoscope imaging device, a process based on a database generated by using a plurality of in-vivo images captured at earlier timings than timings at which the processing target image sequence is captured, and a process that determines, when a bleeding has been occurring inside the living body, a kind of a desirable bleeding stopping treatment for a blood vessel on which the bleeding has been (Continued)

occurring based on the processing target image sequence and the database to present, to a user, the determined type of the bleeding stopping treatment.

14 Claims, 20 Drawing Sheets

(51) Int. Cl.
    *A61B 5/02* (2006.01)
    *G06T 7/00* (2017.01)
    *G16H 20/00* (2018.01)

(52) U.S. Cl.
    CPC ... *G16H 20/00* (2018.01); *G06T 2207/10016* (2013.01); *G06T 2207/10068* (2013.01); *G06T 2207/20081* (2013.01); *G06T 2207/30101* (2013.01)

(58) Field of Classification Search
    CPC . G06T 2207/30101; G06T 2207/20084; A61B 1/00009; A61B 5/02042; A61B 1/045; A61B 5/1459; A61B 1/041; A61B 1/063; A61B 5/0084; A61B 5/073; A61B 1/0684; G16H 20/00; G16H 20/40; G16H 30/40; G16H 50/20

See application file for complete search history.

(56) References Cited

U.S. PATENT DOCUMENTS

| | | | |
|---|---|---|---|
| 2012/0268573 A1* | 10/2012 | Schonborn | A61B 1/051 |
| | | | 348/E13.074 |
| 2014/0031659 A1 | 1/2014 | Zhao et al. | |
| 2014/0296666 A1* | 10/2014 | Rabinovitz | A61B 1/063 |
| | | | 600/310 |
| 2018/0125333 A1 | 5/2018 | Zhao et al. | |
| 2019/0201136 A1* | 7/2019 | Shelton, IV | A61B 1/051 |
| 2020/0054400 A1* | 2/2020 | Hayami | A61B 1/00006 |
| 2020/0069160 A1* | 3/2020 | Oosake | A61B 1/000094 |
| 2020/0138265 A1* | 5/2020 | Endo | G06T 7/0012 |
| 2021/0015432 A1 | 1/2021 | Konno et al. | |
| 2021/0022586 A1* | 1/2021 | Mori | A61B 1/045 |
| 2021/0244260 A1* | 8/2021 | Uyama | G02B 27/646 |
| 2021/0279498 A1* | 9/2021 | Makino | A61B 1/045 |
| 2021/0350570 A1* | 11/2021 | Hibi | G06V 10/764 |
| 2022/0020496 A1* | 1/2022 | Saito | G06T 7/0012 |
| 2022/0071559 A1* | 3/2022 | Jones | A61B 5/0075 |
| 2022/0361950 A1* | 11/2022 | Oh | A61B 18/149 |

\* cited by examiner

FIG. 13

| k | BLEEDING START FRAME | $x_s$ | $y_s$ |
|---|---|---|---|
| 1 | $f_1$ | $x_1$ | $y_1$ |
| 2 | $f_2$ | $x_2$ | $y_2$ |
| ⋮ | ⋮ | ⋮ | ⋮ |

FIG. 14A

| IMAGE SEQUENCE | BLOOD VESSEL TYPE |
|---|---|
|  | PORTAL VEIN |
|  | HEPATIC VEIN |
| ⋮ | ⋮ |

FIG. 14B

| BLOOD VESSEL TYPE | TREATMENT |
|---|---|
| PORTAL VEIN | SUTURING |
| HEPATIC VEIN | CLIPPING |
| ⋮ | ⋮ |

| IMAGE SEQUENCE | BLOOD VESSEL TYPE | TREATMENT |
|---|---|---|
| | PORTAL VEIN | SUTURING |
| | HEPATIC VEIN | CLIPPING |
| | HEPATIC VEIN | BURNING AND SEALING |
| ⋮ | ⋮ | ⋮ |

FIG. 23A

| BLEEDING SPEED | BLOOD VESSEL TYPE |
|---|---|
| (steady graph) | PORTAL VEIN |
| (pulsatile graph) | HEPATIC ARTERY |
| ⋮ | ⋮ |

FIG. 23B

| BLOOD VESSEL TYPE | TREATMENT |
|---|---|
| PORTAL VEIN | SUTURING |
| HEPATIC VEIN | CLIPPING |
| ⋮ | ⋮ |

IMAGE PROCESSING SYSTEM, ENDOSCOPE SYSTEM, AND IMAGE PROCESSING METHOD

CROSS REFERENCE TO RELATED APPLICATION

This application is a continuation of International Patent Application No. PCT/JP2020/006965, having an international filing date of Feb. 21, 2020, which designated the United States, the entirety of which is incorporated herein by reference.

BACKGROUND

In surgery using an endoscope system, conventionally known is a method of performing an image process based on an image captured with the inside of a living body. For example, Japanese Unexamined Patent Application Publication No. 2011-36371 discloses a method of detecting a bleeding region based on movie information during surgery.

SUMMARY

In accordance with one of some aspect, there is provided an image processing system, comprising: at least one processor including hardware, wherein the processor being configured to perform a process that acquires, as a processing target image sequence, images captured in a time series manner with an inside of a living body by an endoscope imaging device, and a process based on the processing target image sequence and a database generated by using a plurality of in-vivo images captured at earlier timings than timings at which the processing target image sequence is captured, and a process that determines, when a bleeding has been occurring inside the living body, a kind of a bleeding stopping treatment desirable for a blood vessel on which the bleeding has been occurring based on the processing target image sequence and the database to present, to a user, the determined type of the bleeding stopping treatment.

In accordance with one of some aspect, there is provided an endoscope system, comprising: an imaging device that captures images of an inside of a living body; and at least one processor including hardware, wherein the processor being configured to perform a process that acquires, as a processing target image sequence, the images captured in a time series manner by the imaging device, a process based on the processing target image sequence and a database generated by using a plurality of in-vivo images captured at earlier timings than timings at which the processing target image sequence is captured, and a process that determines, when a bleeding has been occurring inside the living body, a kind of a bleeding stopping treatment desirable for a blood vessel on which the bleeding has been occurring based on the processing target image sequence and the database to present, to a user, the determined type of the bleeding stopping treatment.

In accordance with one of some aspect, there is provided an image processing method, comprising: performing a process that acquires, as a processing target image sequence, images captured in a time series manner with an inside of a living body by an endoscope imaging device; performing a process that determines, when a bleeding has been occurring inside the living body, a kind of a bleeding stopping treatment desirable for a blood vessel on which the bleeding has been occurring based on the processing target image sequence and a database generated by using a plurality of in-vivo images captured at earlier timings than timings at which the processing target image sequence is captured; and performing a process that presents, to a user, the determined type of the bleeding stopping treatment.

BRIEF DESCRIPTION OF THE DRAWINGS

FIG. 13 illustrates an example of data acquired by the bleeding point detection process.

FIGS. 14A and 14B each illustrate an example of a database.

FIGS. 23A and 23B each illustrate another example of the database.

DESCRIPTION OF EXEMPLARY EMBODIMENTS

Figure 1:
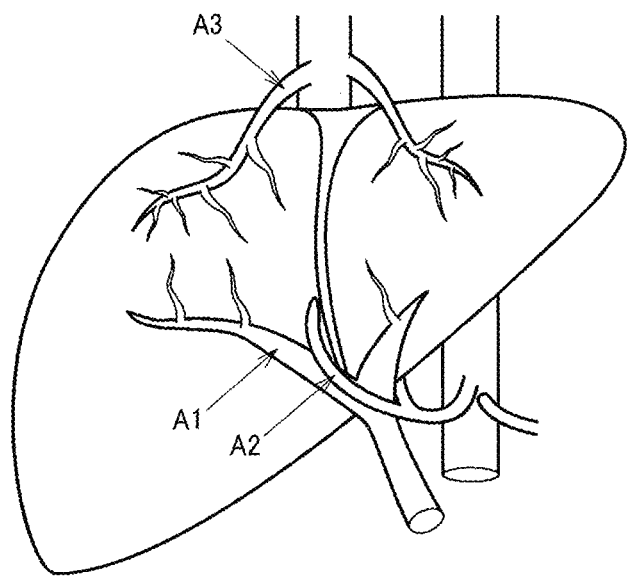
FIG. 1 is a schematic diagram illustrating blood vessels related to the liver.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. Method in Accordance with the Present Embodiment

In surgery using a laparoscope, there is a possibility that an unexpected bleeding occurs during the surgery even if a doctor conducts the surgery in accordance with pre-surgery plan. For example, there is a difference in running of blood vessels among individuals depending on a patient. Thus, it is difficult to infallibly avoid damage on blood vessels. In a case where the bleeding occurs, the doctor needs to perform a treatment promptly. For example, in a case where partial hepatectomy for resecting part of the liver is performed, there is a possibility that an erroneous treatment for the bleeding relates to the prognosis. Thus, it is important to perform the treatment promptly.

For example, Japanese Unexamined Patent Application Publication No. 2011-36371 discloses a method of detecting and presenting information regarding a bleeding based on a captured image. In accordance with a conventional method as disclosed in Japanese Unexamined Patent Application Publication No. 2011-36371 or the like, however, it may be possible to detect presence/absence of the bleeding or the like, but determination of a specific treatment based on the information is left to a doctor.

FIG. 1 is a schematic diagram illustrating the liver and blood vessels related to the liver. As illustrated in FIG. 1, the blood vessels related to the liver include a plurality of blood vessels of different types, a portal vein (A1), a hepatic artery (A2), and a hepatic vein (A3). A desirable bleeding stopping treatment performed when a bleeding has been occurring is different depending on a blood vessel type. For this reason, it is difficult to determine an appropriate treatment for the bleeding promptly depending on the doctor's degree of proficiency. This results in an increase in surgery time and burden on a patient and a surgeon.

Figure 2:
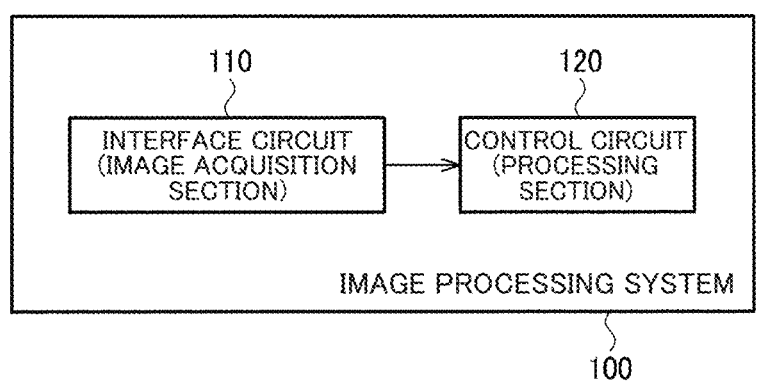
FIG. 2 illustrates a schematic configuration example of an image processing system.

FIG. 2 is a diagram illustrating a configuration example of an image processing system 100 in accordance with the present embodiment. The image processing system 100 includes an image acquisition section 110 and a processing section 120. The image acquisition section 110 acquires, as a processing target image sequence, images captured in a time series manner with the inside of a living body by an endoscope imaging device. The processing section 120 performs processing based on the processing target image sequence and a database that is generated by using a plurality of in-vivo images captured at earlier timings than timings at which the processing target image sequence is captured. The processing section 120 then performs a process that determines, when a bleeding has been occurring inside the living body, a bleeding stopping treatment for a blood vessel on which the bleeding has been occurring based on the processing target image sequence and the database to present, to a user, the determined bleeding stopping treatment. Note that the endoscope imaging device is an imaging device included in an endoscope system 200, and is, for example, arranged in an endoscopic scope 210, which will be described later. When the bleeding has been occurring inside the living body mentioned herein specifically represents a case where the occurrence of the bleeding is detected by a bleeding detection process, which will be described later with reference to FIG. 9. However, the image processing system 100 may execute a determination process that determines a bleeding stopping treatment on a periodic basis without performing the bleeding detection process. In this case, a result of the determination process that determines the bleeding stopping treatment is different in accordance with an occurrence situation of the bleeding. When the bleeding has been occurring, the image processing system 100 determines and presents a specific bleeding stopping treatment such as suturing. When no bleeding has been occurring, the image processing system 100 determines that a bleeding stopping treatment is not necessary.

The processing target image sequence mentioned herein represents images captured in a time series manner serving as a target of the determination process that determines the bleeding stopping treatment. Specifically, the processing target image sequence is a real-time movie captured in laparoscopic surgery being conducted. In contrast, the database includes a plurality of images captured in surgery conducted earlier than an execution timing of the determination process that determines the bleeding stopping treatment. Note that the surgery conducted earlier may target a patient identical to a target patient of the laparoscopic surgery being conducted in real time, or may target a different patient. For example, in a case where a bleeding stopping treatment in partial hepatectomy is determined, the database includes a movie captured in partial hepatectomy conducted in the past. Note that in consideration of a relationship with the processing target image sequence, the surgery mentioned herein is, specifically, surgery using a laparoscope. However, the database may include a case image acquired by capturing of an image of the progress of surgery in laparotomy. In consideration of accuracy in processing based on the database, the database preferably includes a larger amount of information. For example, when a movie in a period corresponding to one-time occurrence of a bleeding in partial hepatectomy is counted as one movie, the database includes a plurality of movies. That is, one movie corresponding to one-time bleeding includes a plurality of in-vivo images, and the database includes the plurality of movies.

The method in accordance with the present embodiment enables not only presentation of presence/absence of a bleeding and a bleeding point, but also presentation of a recommended bleeding stopping treatment to a user. Specifically, the user mentioned herein is a doctor who is a surgeon. This enables appropriate support for the bleeding stopping treatment performed by the user.

Note that in an in-vivo image, a region in which blood exists is captured as a red region. For this reason, a bleeding amount can be estimated based on an area of the red region. However, when a distance between an imaging section and the living body is changed, a size of an object, which has an identical actual size, is changed on an image. In addition, a configuration of an imaging optical system such as a lens and an image process such as digital zooming become a factor for changing a size of a given object on the image. For this reason, it is not easy to correctly grasp a bleeding state only from the processing target image sequence, for example, to accurately estimate a bleeding amount and a time-series change in the bleeding amount. Hence, it is also difficult to accurately estimate a recommended bleeding stopping treatment for the bleeding only from the processing target image sequence. For example, even if an attempt is made to determine a bleeding stopping treatment by such a process as that compares a given threshold and the area of the red region, an appropriate threshold cannot be set. In addition, there is a difference in size or detailed shape of an organ such as the liver among individuals depending on a patient. Also from this point, it can be said that setting a threshold that can be applied to many patients for a general purpose is difficult.

In contrast, the method in accordance with the present embodiment, in determination of the recommended bleeding stopping treatment, is to perform the processing based on the database, instead of using only the processing target image sequence. Since the processing based on information acquired in surgery conducted earlier is performed, it is possible to accurately estimate the recommended bleeding stopping treatment. Note that the processing based on the database may be processing based on a trained model generated by machine learning using the database, or may be a comparison process using information included in the database and the processing target image sequence. Details will be described later.

2. System Configuration Example

First, a configuration of the whole system including the image processing system 100 will be described first, and thereafter a detailed configuration of the image processing system 100 and a configuration of the endoscope system 200 will be described.

2.1 Overall Configuration Example

Figure 3:
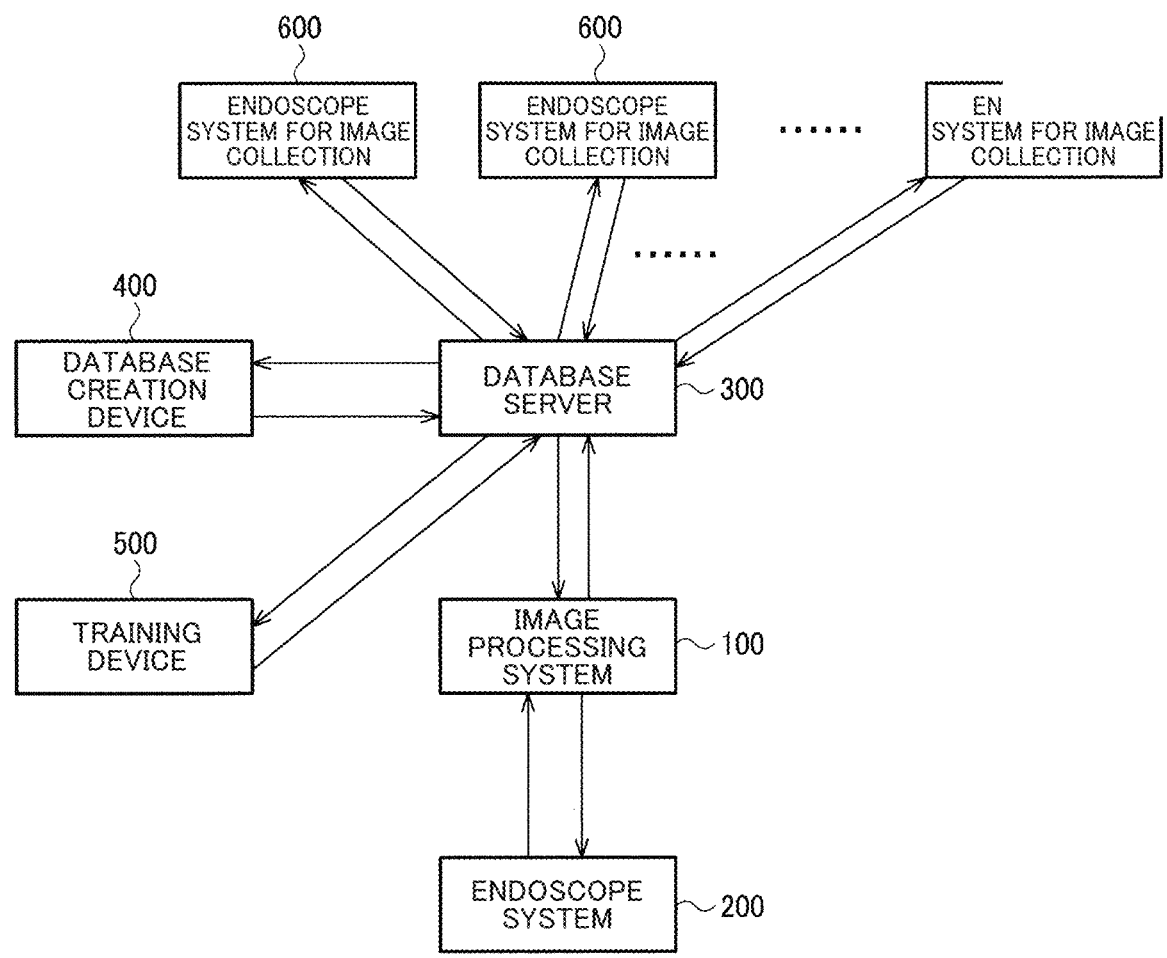
FIG. 3 illustrates a configuration example of a system including the image processing system.

FIG. 3 illustrates a configuration example of a system including the image processing system 100 in accordance with the present embodiment. As illustrated in FIG. 3, the system includes the image processing system 100, the endoscope system 200, a database server 300, a database creation device 400, a training device 500, and an endoscope system for image collection 600. Note that a configuration of the system is not limited to that illustrated in FIG. 3, and can be modified in various manners such as omission of part of constituent elements and addition of another constituent element.

The endoscope system for image collection 600 is an endoscope system that captures a plurality of in-vivo images for creating the database in accordance with the present embodiment. In contrast, the endoscope system 200 is a system that captures the processing target image sequence serving as a target of the process that determines the bleeding stopping treatment, and a system in which surgery using a laparoscope is being conducted in a more limited sense. In consideration of an update process that updates the database, which will be described later, the processing target image sequence captured by the endoscope system 200 can be used as part of the database for determining a bleeding stopping treatment in future surgery. That is, the endoscope system 200 may function as the endoscope system for image collection 600 at another timing. Additionally, the endoscope system for image collection 600 may function as the endoscope system 200 in accordance with the present embodiment at another timing.

The database server 300 may be a server arranged in a private network such as an intranet, or may be a server arranged in a public telecommunication network such as the Internet.

The database server 300 first collects a surgery image sequence, which is a plurality of in-vivo images acquired during surgery conducted earlier, from the endoscope system for image collection 600. However, the surgery image sequence also includes images not related to a bleeding or other images. For example, an image captured in a period in which no bleeding has been occurring among the surgery image sequence is less useful for the process that determines the bleeding stopping treatment than an image captured when the bleeding has been occurring. The plurality of in-vivo images captured with a bleeding needs to be associated with information regarding a bleeding stopping treatment that should be performed for the bleeding for being utilized for the process that determines the bleeding stopping treatment in the image processing system 100.

Hence, the database creation device 400 performs a process that acquires the surgery image sequence collected by the database server 300 from the endoscope system for image collection 600 and creates the database in accordance with the present embodiment.

Figure 4:
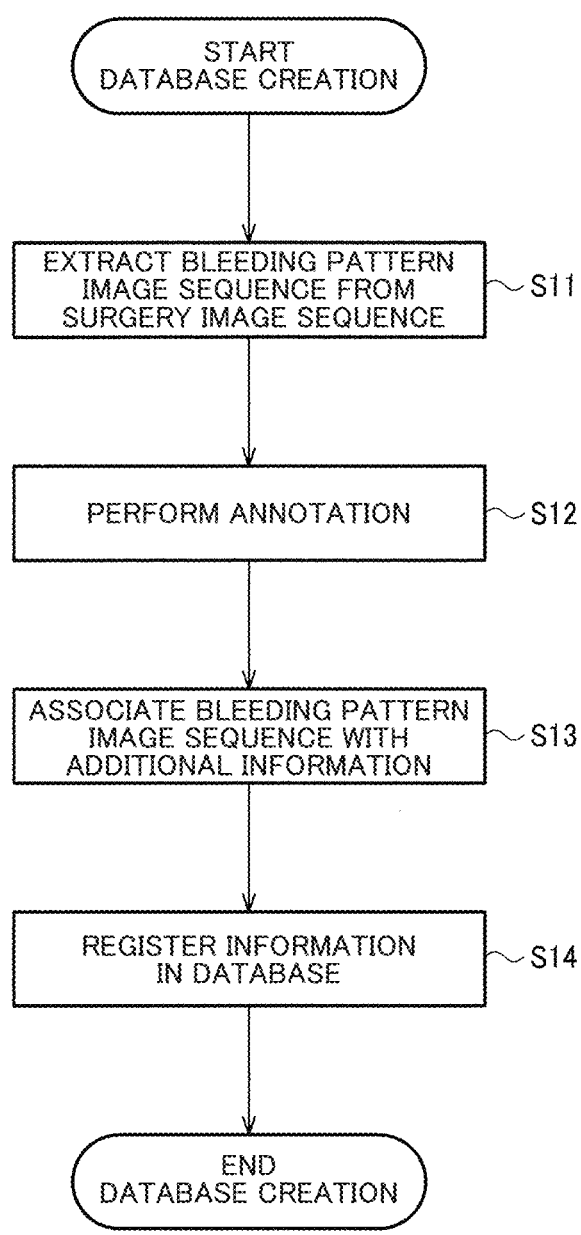
FIG. 4 is a flowchart describing a database creation process.

FIG. 4 is a flowchart describing the process that creates the database in the database creation device 400. When this process is started, in step S11, the database creation device 400 performs a process that extracts a bleeding pattern image sequence from the surgery image sequence. The bleeding pattern image sequence represents, for example, a plurality of in-vivo images corresponding to a period from a bleeding start frame to a frame in which the bleeding is detected. For example, the database creation device 400 executes a process, which will be described later with reference to FIGS. 9 to 11, and thereby performs a process that identifies an image Pi in which the bleeding is detected and an image Ps corresponding to the bleeding start frame. The database creation device 400 extracts images corresponding to the period from Pi to Ps as the bleeding pattern image sequence. Note that all of the images corresponding to the period from Pi to Ps may be an extraction target, or part of the images may be omitted. Alternatively, the bleeding pattern image sequence represents, for example, a plurality of in-vivo images corresponding to a period from the start of the bleeding to execution of an emergency bleeding stopping treatment. In this case, it is assumed that the bleeding amount increases from a start timing over time, and decreases when the emergency bleeding stopping treatment is started. In this manner, the database creation device 400 preliminarily defines a time-series change in bleeding state in in-vivo images as a bleeding pattern, and then performs a process that extracts an image sequence having higher similarity to the bleeding pattern from the surgery image sequence. Note that the image sequence may be extracted based on user's input, or may be automatically extracted using an image process.

Subsequently, in step S12, the database creation device 400 performs annotation. The annotation is a process that adds metadata regarding a recommended bleeding stopping treatment for a bleeding whose image has been captured in the bleeding pattern image sequence. The annotation is performed by, for example, a user who has expert knowledge, such as a doctor. The database creation device 400 accepts input of annotation performed by the user, and performs a process that associates the image sequence extracted in step S11 with the accepted information. Note that the information added herein may be information that identifies a bleed vessel type, information that identifies a bleeding stopping treatment, or information that identifies both of the bleed vessel type and the bleeding stopping treatment.

Additionally, in step S13, the database creation device 400 may perform a process that associates the bleeding pattern image sequence with another additional information. The additional information mentioned herein may include information of a surgeon, an operative method, and a hospital name, information of an item to which attention should be paid during the surgery, and other information. In addition, the additional information may be information regarding a patient such as age, sex, height, and weight, or information acquired using computed tomography (CT) or magnetic resonance imaging (MRI).

In step S14, the database creation device 400 performs a process that registers information in which the bleeding pattern image sequence is associated with the metadata including the information for identifying the bleeding stopping treatment in the database in accordance with the present embodiment. The process in step S14 is, specifically, a process that writes table data in the database server 300.

The training device 500 performs machine learning using the database to generate a trained model. For example, the training device 500 acquires the database from the database server 300, and performs machine learning, which will be described later, to generate the trained model. The training device 500 transmits the generated trained model to the database server 300.

The image processing system 100 acquires the trained model from the database server 300. In addition, the image processing system 100 acquires the processing target image sequence from the endoscope system 200. The image processing system 100 then performs the process that determines the bleeding stopping treatment based on the trained model generated based on the database and the processing target image sequence.

Note that the database creation device 400 is included in the database server 300, and the processing described in the FIG. 4 may be performed in the database server 300. Alternatively, the database creation device 400 may be included in the endoscope system for image collection 600. In this case, the processing described in FIG. 4 is executed in the endoscope system for image collection 600, and data after the processing is transmitted to the database server 300.

Additionally, the database creation device 400 and the training device 500 may be an identical device. In this case, the process that creates the database from the surgery image sequence and the machine learning based on the created database can be executed in the identical device. Alternatively, the training device 500 and the image processing system 100 may be configured in an integrated manner. In this case, a training process that generates the trained model and an inference process using the trained model can be executed in the identical device.

While FIG. 3 illustrates the example in which the trained model generated by the training device 500 is temporarily accumulated in the database server 300, the trained model may be directly transmitted from the training device 500 to the image processing system 100. As described later, the machine learning is not essential for the method in accordance with the present embodiment. In a case where the machine learning is not performed, the training device 500 can be omitted.

As described above, FIG. 3 illustrates one example of the configuration of the system, and the configuration of the system including the image processing system 100 can be modified in various manners.

2.2 Image Processing System

Figure 5:
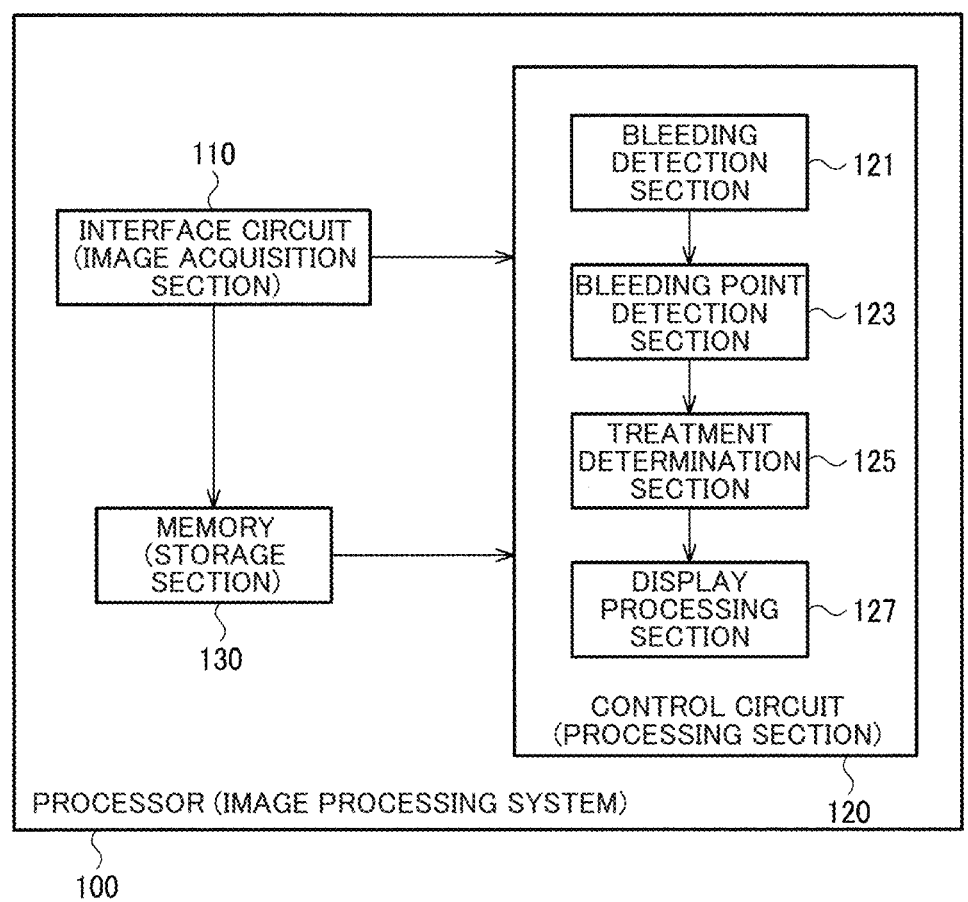
FIG. 5 illustrates a configuration example of the image processing system.

FIG. 5 is a diagram illustrating a detailed configuration example of the image processing system 100. The image processing system 100 includes an image acquisition section 110, a processing section 120, and a storage section 130. The processing section 120 includes a bleeding detection section 121, a bleeding point detection section 123, a treatment determination section 125, and a display processing section 127. Note that a configuration of the image processing system 100 and a configuration of the processing section 120 are not limited to those illustrated in FIG. 5, and can be modified in various manners such as omission of part of constituent elements and addition of another constituent element.

The image acquisition section 110 is an interface circuit that acquires an in-vivo image captured by an imaging device of the endoscope system 200. In a case where the image processing system 100 is included in a processor unit 220 of the endoscope system 200, the image acquisition section 110 corresponds to a captured image data reception section 221 that acquires an image signal from the imaging device via a cable. The interface circuit is, for example, a circuit that has a function of acquiring an in-vivo image from the endoscope system 200, and transmitting the acquired in-vivo image to the processing section 120. In this case, the image acquisition section 110 may receive the in-vivo image, which is digital data, from the imaging device. Alternatively, the image acquisition section 110 may receive an analog signal from the imaging device, perform analog/digital (A/D) conversion on the analog signal, and thereby acquire the in-vivo image, which is digital data. That is, the interface circuit may be an A/D conversion circuit. Additionally, in a case where the image processing system 100 is arranged separately from the endoscope system 200, the image acquisition section 110 is implemented as a communication interface that receives the in-vivo image via a network from the endoscope system 200. That is, the interface circuit may be a communication chip or a circuit arranged in a communication device. The network mentioned herein may be a private network such as an intranet, or may be a public telecommunication network such as the Internet. The network may be a wired network or a wireless network. The image acquisition section 110, for example, acquires images captured with the inside of the living body for each frame. Alternatively, the image acquisition section 110 may collectively acquire a plurality of images corresponding to a plurality of frames.

The processing section 120 is composed of the following hardware. The hardware can include at least one of a control circuit that processes a digital signal or a control circuit that processes an analog signal. For example, the hardware can be composed of one or more circuit devices mounted on a circuit board, or one or more circuit elements. The one or more circuit devices are, for example, integrated circuits (ICs), field-programmable gate array (FPGA) circuits, or the like. The one or more circuit elements are, for example, resistors, capacitors, or the like.

In addition, the processing section 120 may be implemented by the following processor. The image processing system 100 includes a memory that stores information, and a processor that operates based on the information stored in the memory. The memory mentioned herein may be the storage section 130, or a different memory. The information is, for example, a program and various kinds of data or the like. The processor includes hardware. Note that various kinds of processors such as a central processing unit (CPU), a graphics processing unit (GPU), and a digital signal processor (DSP) can be used. The memory may be a semiconductor memory such as a static random-access memory (SRAM) and a dynamic random-access memory (DRAM). The memory may be a register. The memory may be a magnetic storage device such as a hard disk drive (HDD). The memory may be an optical storage device such as an optical disk device. For example, the memory stores a computer-readable instruction. The instruction is executed by the processor, whereby respective functions of the sections included in the processing section 120 are implemented. The sections of the processing section 120 are, specifically, the bleeding detection section 121, the bleeding point detection section 123, the treatment determination section 125, and the display processing section 127. The instruction mentioned herein may be an instruction of an instruction set that is included in a program, or may be an instruction that instructs a hardware circuit included in the processor to operate. Furthermore, all or part of the sections of the processing section 120 can be implemented by cloud computing, and each process, which will be described later, can be executed on the cloud computing.

The storage section 130 serves as a work area of the processing section 120 or the like, and can be implemented by a semiconductor memory, a resistor, a magnetic storage device, or the like. The storage section 130 stores the processing target image sequence acquired by the image acquisition section 110. The storage section 130 also stores the trained model generated using the database. Note that the storage section 130 may store the database itself together with the trained model, or may store the database itself instead of the trained model.

The bleeding detection section 121 performs a bleeding detection process that detects whether or not a bleeding has been occurring inside the living body serving as an imaging target based on the processing target image sequence. Details of the bleeding detection process will be described later with reference to FIG. 9.

The bleeding point detection section 123 performs a bleeding point detection process that detects a bleeding point based on the processing target image sequence. The bleeding point mentioned herein represents a position at which the bleeding has been occurring. Details of the bleeding point detection process will be described later with reference to FIGS. 10 and 11.

The treatment determination section 125 performs a process that determines a recommended bleeding stopping treatment for the bleeding. The treatment determination section 125 performs, for example, a process that reads out the trained model from the storage section 130, a process that inputs, to the trained model, an image sequence obtained by extracting a predetermined section from the processing target image sequence, a process that determines a blood vessel type of a blood vessel on which the bleeding has been occurring based on output from the trained model, and a process that determines a bleeding stopping treatment based on the determined bleed vessel type. Details of the processes using the trained model will be described later with reference to FIGS. 14A to 17. Note that, as described later as a modification, the processing section 120 may directly determine the bleeding stopping treatment based on the output from the trained model. Alternatively, the processing section 120 may determine the bleeding stopping treatment based on a comparison process that compares the processing target image sequence and the database without using the trained model.

The display processing section 127 performs a process that displays the bleeding stopping treatment determined by the treatment determination section 125 on a display section. The display section mentioned herein is, for example, a display section 230 of the endoscope system 200. The display processing section 127 performs, for example, a process that superimposes information regarding the bleeding stopping treatment on each image of the processing target image sequence to generate a display image, and a process that transmits the generated display image to the display section 230. Alternatively, the display processing section 127 may perform a process that transmits the display image to the processor unit 220 of the endoscope system 200. In this case, display control in the display section 230 is executed by the processor unit 220. Additionally, the display process performed by the display processing section 127 may be a process that transmits the information regarding the determined bleeding stopping treatment to a device of the endoscope system 200 or the like and instructs display. In this case, the process that generates the display image and the process that controls the display section 230 are executed by the processor unit 220.

The processing executed by the image processing system 100 in accordance with the present embodiment may be implemented as an image processing method. The image processing method in accordance with the present embodiment includes the process that acquires, as the processing target image sequence, images captured in a time series manner with the inside of the living body by the endoscope imaging device, the process that determines, when the bleeding has been occurring inside the living body, the bleeding stopping treatment on the blood vessel on which the bleeding has been occurring based on the processing target image sequence and the database generated by using the plurality of in-vivo images captured at earlier timings than timings at which the processing target image sequence is captured, and the process that presents the determined bleeding stopping treatment to the user.

Additionally, each section of the processing section 120 in accordance with the present embodiment may be implemented as a module of a program that operates on a processor. For example, the bleeding detection section 121 and the bleeding point detection section 123 are implemented as an image processing module that performs the bleeding detection process and an image processing module that performs the bleeding point detection process, respectively. The treatment determination section 125 is implemented as a processing module for determining the bleeding stopping treatment. In a case where the trained model is used, the treatment determination section 125 is implemented as an inference processing module for calculating output in accordance with the trained model. In a case where the database itself is used, the treatment determination section 125 is implemented as a comparison processing module that compares the processing target image sequence and the database. The display processing section 127 is implemented as an image processing module that generates the display image or a control module that controls the display section 230.

A program that implements processing that is performed by each section of the processing section 120 in accordance with the present embodiment can be stored, for example, in an information storage device, which is a computer-readable medium. The information storage device can be implemented by, for example, an optical disk, a memory card, a hard disk drive (HDD), a semiconductor memory, or the like. The semiconductor memory is, for example, a read-only memory (ROM). The processing section 120 performs various kinds of processing in accordance with the present embodiment based on the program stored in the information storage device. That is, the information storage device stores the program for causing a computer to function as each section of the processing section 120. The computer is a device provided with an input device, a processing section, a storage section, and an output section. Specifically, the program in accordance with the present embodiment is a program for causing the computer to execute each step, which will be described later with reference to FIG. 7 or the like.

2.3 Endoscope System

Figure 6:
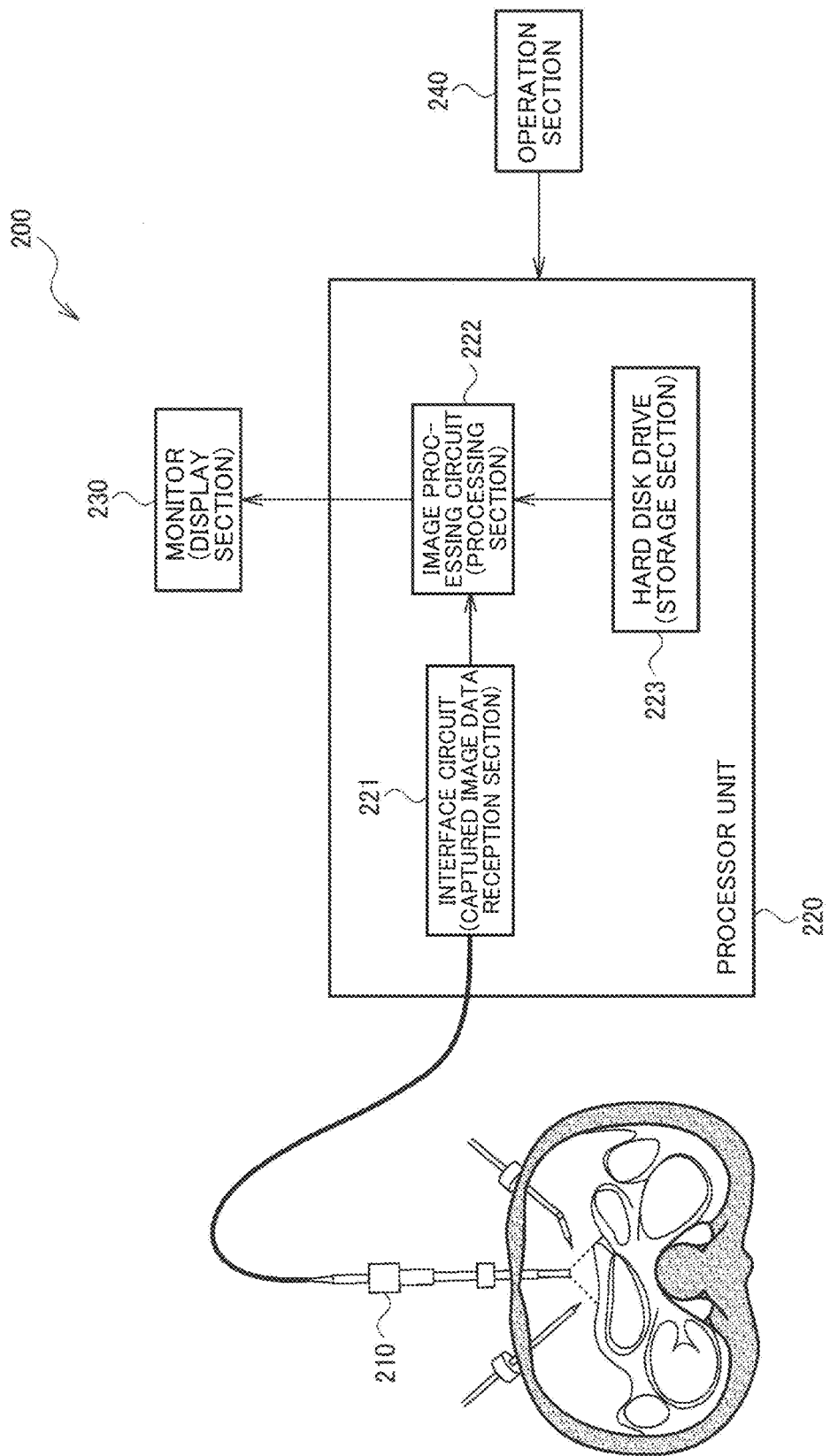
FIG. 6 illustrates a configuration example of an endoscope system.

FIG. 6 illustrates a configuration example of the endoscope system 200. The endoscope system 200 includes the endoscopic scope 210, the processor unit 220, and the display section 230. The endoscope system 200 may further include an operation section 240.

An imaging device is arranged at a leading end portion of the endoscopic scope 210, and the leading end portion is inserted into an abdominal cavity. The imaging device captures an image of the abdominal cavity, and captured image data is transmitted from the endoscopic scope 210 to the processor unit 220.

The processor unit 220 is a device that performs various kinds of processing in the endoscope system 200. For example, the processor unit 220 performs control of the endoscope system 200, an image process, and the like. The processor unit 220 includes the captured image data reception section 221, a processing section 222, and a storage section 223.

The captured image data reception section 221 receives captured image data from the endoscopic scope 210. The captured image data reception section 221 is, for example, a connector to which a cable of the endoscopic scope 210 is connected, an interface circuit that receives captured image data, or the like.

The processing section 222 performs a process on captured image data, and a process that displays a result of the process on the display section 230. The process performed in the processing section 222 is, for example, a correction process such as a white balance process and a noise reduction process. In addition, the processing section 222 may perform a detection process that detects a given object from the captured image data, or other processes. The processing section 222 mentioned herein is, specifically, an image processing circuit.

The storage section 223 serves as a work area of the processing section 222 or the like, and is, for example, a storage device such as a semiconductor memory, a hard disk drive, and an optical disk drive.

The display section 230 is a monitor that displays an image output from the processing section 222, and is, for example, a display device such as a liquid crystal display and an organic electroluminescence (EL) display.

The operation section 240 is a device for an operator to operate the endoscope system 200. The operation section 240 is, for example, a button, a dial, a foot switch, a touch panel, or the like. As described later, the processing section 222 may change a display mode of an object based on input information from the operation section 240.

The image processing system 100 illustrated in FIGS. 2 and 5 may be, for example, arranged separately from the endoscope system 200 illustrated in FIG. 6. For example, the image processing system 100 is included in an information processing device connected to the processor unit 220. The information processing device mentioned herein may be a personal computer (PC), or a server system. The processor unit 220 and the information processing device may be connected to each other by a cable or may be connected to each other using a wireless network.

The processing section 222 of the processor unit 220 performs a process that transmits captured image data acquired by the captured image data reception section 221 to the information processing device via a communication section, which is not illustrated. The image acquisition section 110 of the image processing system 100 acquires captured image data that is captured in a time-series manner and that is transmitted from the processor unit 220, as the processing target image sequence. The processing section 120 performs a determination process that determines a bleeding stopping treatment on the processing target image sequence. The image processing system 100 returns a result of the determination process that determines the bleeding stopping treatment to the processor unit 220. The processing section 222 of the processor unit 220 displays, on the display section 230, a display image including information regarding the bleeding stopping treatment and received from the image processing system 100.

Alternatively, the image processing system 100 may be included in the endoscope system 200. In this case, the image acquisition section 110 corresponds to the captured image data reception section 221. The processing section 120 corresponds to the processing section 222. The storage section 130 corresponds to the storage section 223. That is, the method in accordance with the present embodiment may be applied to the endoscope system 200. The endoscope system 200 in accordance with the present embodiment includes the imaging section, the image acquisition section 110, and the processing section 120. The imaging section captures an image of the inside of the living body. The image acquisition section 110 acquires, as the processing target image sequence, images captured in a time series manner by the imaging section. The processing section performs processing on the processing target image sequence based on the database generated by using a plurality of in-vivo images captured at earlier timings than timings at which the processing target image sequence is captured. The processing section 120 then performs a process that determines, when a bleeding has been occurring inside the living body, a bleeding stopping treatment for a blood vessel on which the bleeding has been occurring based on the processing target image sequence and the database to present, to the user, the determined bleeding stopping treatment.

The imaging section is, for example, the imaging device included in the endoscopic scope 210, as described above. The endoscopic scope 210 emits, toward the object, illumination light that has been emitted from a light source device, which is not illustrated, that has passed through a light guide, and that has been guided to a illumination lens of the endoscopic scope 210. The imaging section is an image sensor that receives light reflected on the object via a lens system including an objective lens, a focus lens, and the like. Note that the imaging section may include an A/D conversion circuit that converts an analog signal, which is output from the image sensor, to a digital signal. Alternatively, the captured image data reception section 221 may include the A/D conversion circuit.

3. Details of Processing

Subsequently, the processing executed in the image processing system 100 is described. The flow of the overall processing will be described first, and then details of each process will be described.

3.1 Overall Processing

Figure 7:
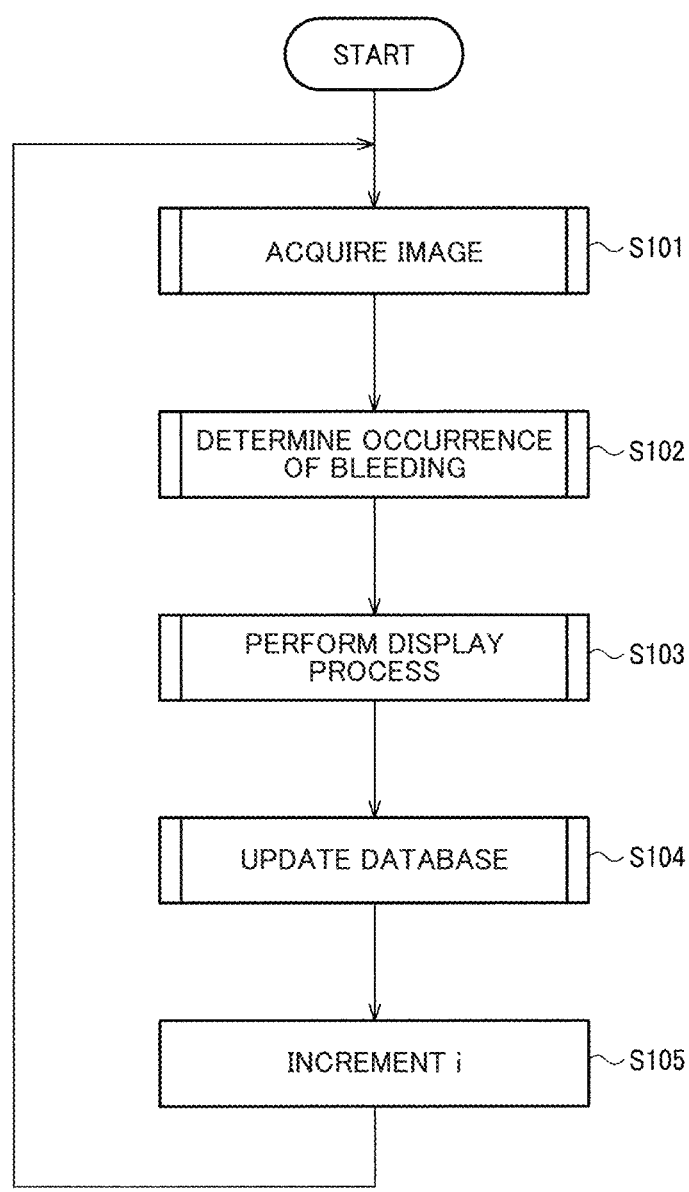
FIG. 7 is a flowchart describing a process executed in the image processing system.

FIG. 7 is a flowchart describing the processing in the image processing system 100. When this processing is started, in step S101, the image acquisition section 110 first acquires a processing target image sequence. For example, the image acquisition section 110 acquires images in the latest frame from the endoscope system 200, and also reads out images for predetermined past frames stored in the storage section 130. The latest frame is denoted as a frame i, and an image in the frame i is denoted as Pi, where i is a variable representing a frame.

In step S102, the processing section 120 performs a bleeding determination process that makes determination regarding a bleeding. The bleeding determination process includes a bleeding detection process performed by the bleeding detection section 121, a bleeding point detection process performed by the bleeding point detection section 123, and a treatment determination process performed by the treatment determination section 125.

In step S103, the display processing section 127 superimposes information regarding an identified bleeding point on the image in the latest frame to generate a display image and performs a process to display the display image on the display section. Additionally, in step S103, the display processing section 127 may display information regarding a determined bleeding stopping treatment.

Subsequently, in step S104, the processing section 120 performs a process that updates the database. Note that the process in step S104 is not necessarily performed during the surgery, and may be executed, for example, after completion of the surgery.

Subsequently, in step S105, after the variable i representing a frame is incremented, the processing returns to step S101. That is, the processes in steps S101 to S104 continue to be performed on an image in the next frame.

3.2 Bleeding Determination Process

Figure 8:
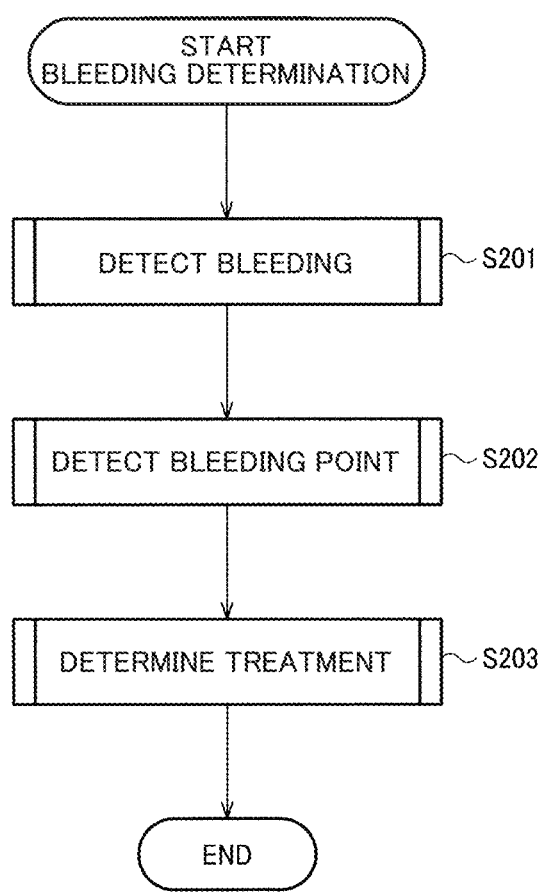
FIG. 8 is a flowchart describing a bleeding determination process.

FIG. 8 is a flowchart describing the bleeding determination process in step S102 in FIG. 7. When this process is started, in step S201, the bleeding detection section 121 performs the bleeding detection process. In step S202, the bleeding point detection section 123 performs the bleeding point detection process. In step S203, the treatment determination section 125 performs the determination process that determines a bleeding stopping treatment. Details of the process in each step will be described below.

3.2.1 Bleeding Detection Process

Figure 9:
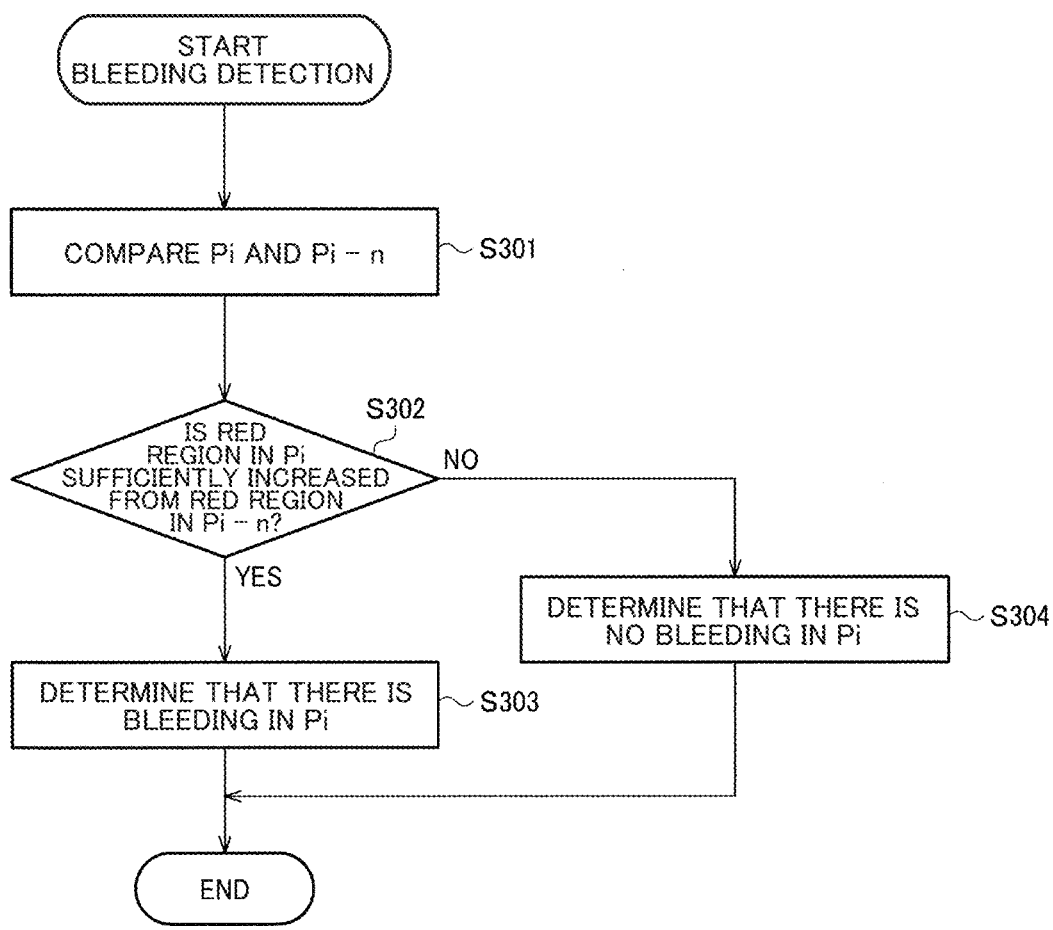
FIG. 9 is a flowchart describing a bleeding detection process.

FIG. 9 is a flowchart describing the bleeding detection process in step S201. First, in step S301, the bleeding detection section 121 performs a comparison process that compares the image Pi, which is a processing target, and an image Pi-n that has been captured earlier by n frames than when Pi is captured. The image Pi-n is, for example, an image acquired one second earlier than acquisition of the image Pi, but a timing of acquisition of an image serving as a comparison target can be modified in various manners.

Subsequently, in step S302, the bleeding detection section 121 determines whether or not a change in a red region between images is large. For example, the bleeding detection section 121 uses a publicly-known matching method such as block matching to identify a changed region between the images. In a case where an area of the changed region is a predetermined value or greater, the bleeding detection section 121 determines whether or not the region is the red region. The bleeding detection section 121 determines, for example, a region in which a hue is within a predetermined angle range including zero degrees as the red region.

When determining that the area of the changed region between the images is the threshold or greater, and that the region is the red region, in step S303, the bleeding detection section 121 determines that there is a bleeding in the image Pi. In other cases, in step S304, the bleeding detection section 121 determines that there is no bleeding in the image Pi.

3.2.2 Bleeding Point Detection Process

Figure 10:
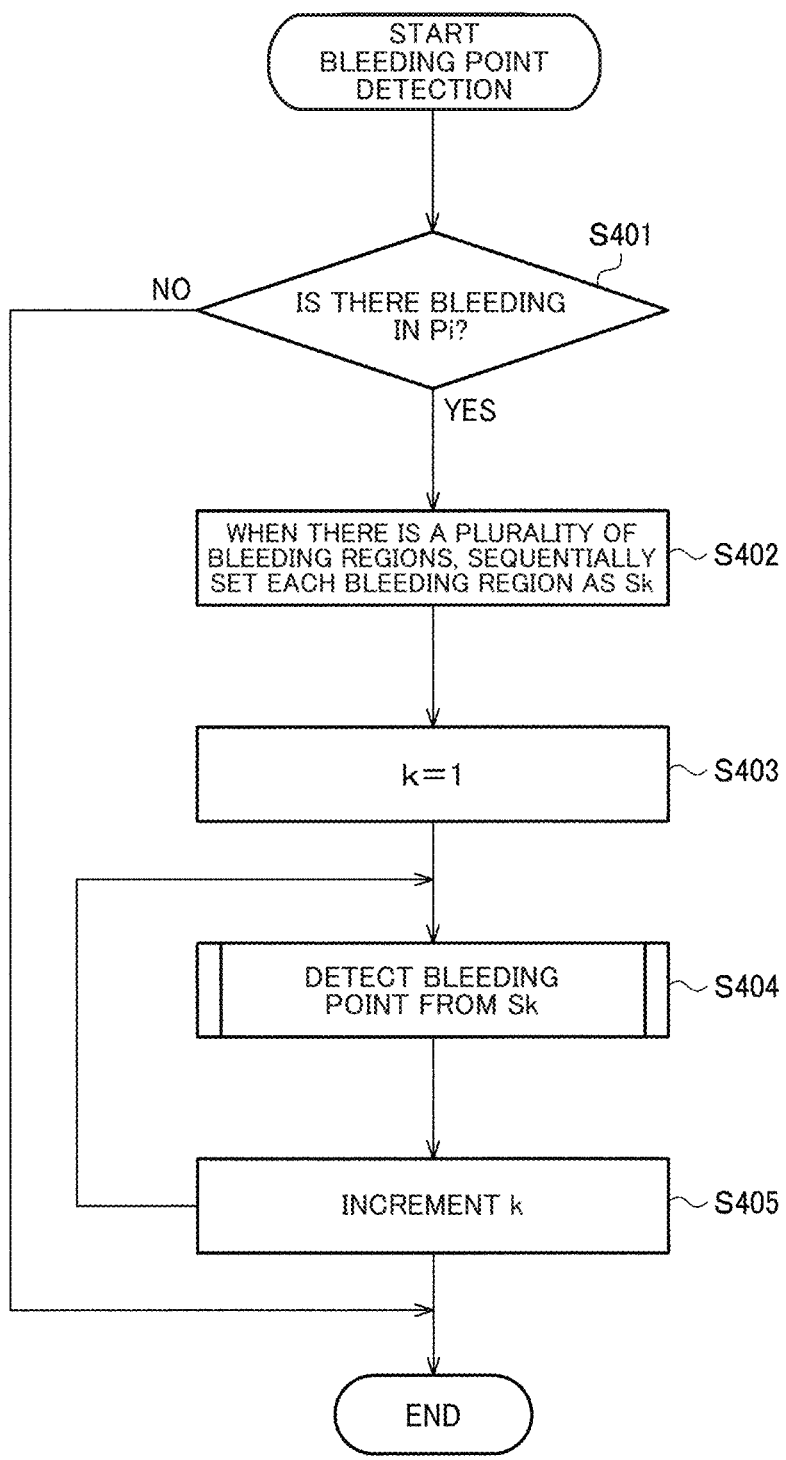
FIG. 10 is a flowchart describing a bleeding point detection process.
Figure 11:
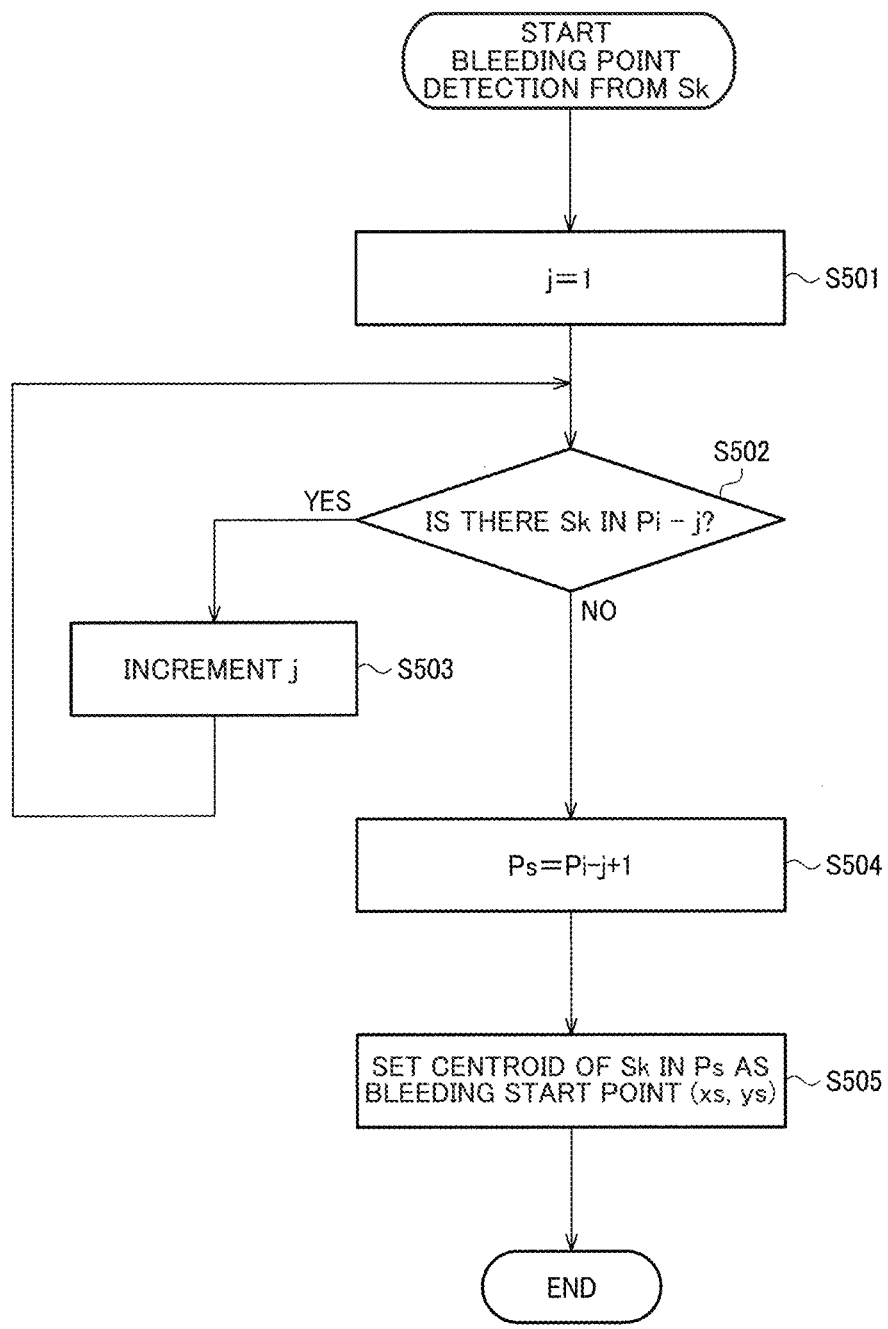
FIG. 11 is a flowchart describing the bleeding point detection process on a given bleeding region.

FIGS. 10 and 11 are flowcharts each describing the bleeding point detection process in step S202. First, in step S401 in FIG. 10, the bleeding point detection section 123 determines whether or not the bleeding is detected on the image Pi. In a case of NO in step S401, the bleeding point detection section 123 ends the processing without performing a process in step S402 or subsequent steps.

In a case of YES in step S401, in step S402, the bleeding point detection section 123 identifies a bleeding region S in the image Pi. The bleeding region mentioned herein is, for example, a region having a predetermined number or more of pixels out of a region that is a set of continuous red regions in the image Pi. Note that in a case where a plurality of bleeding regions exists in the image Pi, the bleeding point detection section 123 distinguishes each bleeding region as S1, S2, . . . .

In step S403, the bleeding point detection section 123 initializes a variable k that identifies the bleeding region with 1. In step S404, the bleeding point detection section 123 executes the bleeding point detection process on a bleeding region Sk. In step S405 after the process in in step S404, the bleeding point detection section 123 increments k, and returns to the process in step S404. That is, the bleeding point detection section 123 sequentially executes the bleeding point detection process on one or more bleeding regions detected in the image Pi. When the bleeding point detection process on all of the bleeding regions is completed, the processing illustrated in FIG. 10 ends.

FIG. 11 is a flowchart describing the bleeding point detection process on the bleeding region Sk in step S404. In step S501, the bleeding point detection section 123 initializes a variable j for searching for a bleeding point with 1. In step S502, the bleeding point detection section 123 determines whether or not there is the bleeding region Sk serving as a processing target in an image Pi-j that has been captured earlier by j frames than when the image Pi is captured. For example, the bleeding point detection section 123 detects a bleeding region in the image Pi-j, obtains a centroid of the bleeding region, and performs a comparison process that compares the centroid and a centroid of Sk in an image Pi-j+1. In a case where a difference is a predetermined threshold or less, the bleeding point detection section 123 determines that the bleeding region in the image Pi-j is the bleeding region Sk serving as the processing target. Note that when it is assumed that movement of the object on images in a period corresponding to one frame is large, the bleeding point detection section 123 may perform correction with a motion vector and then perform the comparison process that compares the centroids.

In a case of YES in step S502, in step S503, the bleeding point detection section 123 increments the variable j. After the process in step S503, the bleeding point detection section 123 returns to step S502 again and continues the processing. That is, the bleeding point detection section 123 determines presence/absence of the bleeding region Sk in a more retrospective manner.

Figure 12A:
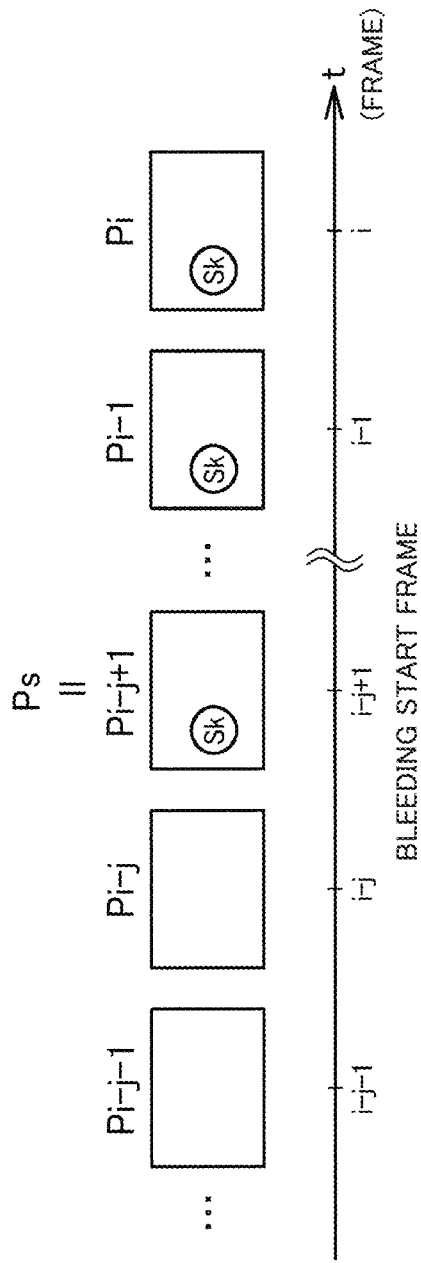
FIGS. 12A and 12B are schematic diagrams for describing the bleeding point detection process.

FIG. 12A is a schematic diagram describing the bleeding point detection process. As illustrated in FIG. 12A, the bleeding point detection section 123 retrospectively searches for the bleeding region Sk detected in the image Pi. FIG. 12A illustrates a case of NO in step S502, that is, a case where Sk is detected in the image Pi-j+1, and Sk is not detected in the image Pi-j. In this case, in step S505, the bleeding point detection section 123 sets the image Pi−j+1 as a bleeding start image Ps corresponding to the bleeding start frame. That is, the bleeding start frame is a frame that has been captured earlier by j−1 frames than capturing of the latest frame i.

Figure 12B:
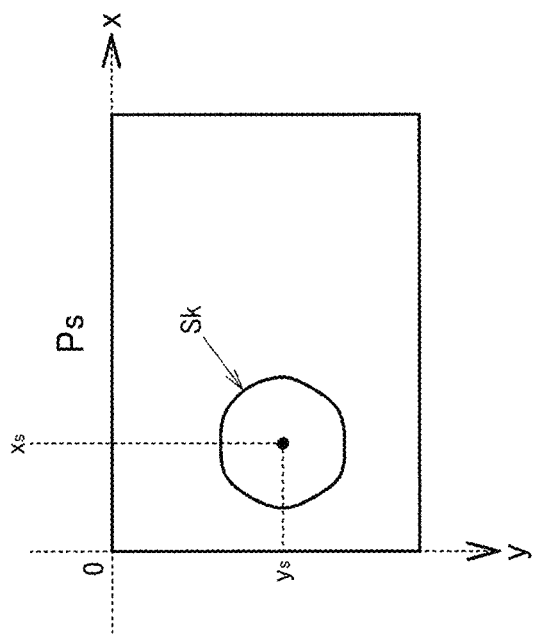

When the bleeding start image Ps is identified, in step S505, the bleeding point detection section 123 identifies a bleeding point. FIG. 12B is a schematic diagram describing a process that identifies a bleeding point (xs, ys). As illustrated in FIG. 12B, the bleeding point detection section 123 performs a process that detects (xs, ys), which is the centroid of the bleeding region Sk, in the image Ps as the bleeding point. While an end point on the upper left of the image is an origin in FIG. 12B, a coordinate system can be freely set.

FIG. 13 is a diagram for describing a configuration of data acquired by the bleeding point detection process illustrated in FIGS. 10 to 12B. As illustrated in FIG. 13, one or more bleeding regions are detected based on the image Pi in the frame i, and each bleeding region is associated with information that identifies the bleeding start frame. The bleeding start frame is, for example, i−j+1, as illustrated in FIG. 11, and a specific numeric value is identified. As illustrated in FIG. 12B, each bleeding region is associated with (xs, ys) that are coordinates identifying the bleeding start point.

As described above, the processing section 120 performs, based on the processing target image sequence, the bleeding detection process that detects whether or not the bleeding has been occurring inside the living body. The processing section 120 then performs, when the bleeding is detected, the bleeding point detection process that identifies the bleeding point, which is an occurrence position of the bleeding. This enables detection of occurrence of the bleeding and identification of the bleeding point, and thereby enables appropriate support for the bleeding stopping treatment performed by the user.

3.2.3 Determination Process that Determines Bleeding Stopping Treatment

The determination process that determines the bleeding stopping treatment in step S203 is now described. Note that a description is also given of a specific example of the database and a training process using the database as a precondition for the determination process that determines the bleeding stopping treatment.

The following description is given of an example in which the processing target image sequence and the in-vivo images included in the database are images captured with the liver. The processing section 120 determines, based on the processing target image sequence and the database, the bleeding stopping treatment for a blood vessel of any one of a hepatic artery, a hepatic vein, and a portal vein. This enables appropriate support for the user to cope with an unexpected bleeding in surgery targeting the liver such as partial hepatectomy. A bleeding is likely to occur especially in the liver because of denseness of blood vessels, and there is a possibility for adverse prognosis unless an appropriate bleeding stopping treatment is performed. For this reason, support for the bleeding stopping treatment regarding the liver is highly useful.

The processing section 120 may identify a bleed vessel type of a blood vessel on which the bleeding has been occurring, based on the processing target image sequence and the database, and determine a bleeding stopping treatment based on the identified type. Accordingly, identifying the bleed vessel type of the blood vessel on which the bleeding has been occurring enables presentation of an appropriate bleeding stopping treatment in accordance with the type to the user.

The bleed vessel type mentioned herein represents, for example, a structural classification in fields of anatomy, angiology, and the like, or a functional classification. As blood vessel types regarding the liver, three types, that is, the portal vein, the hepatic artery, and the hepatic vein, can be assumed as exemplified in FIG. 1. The portal vein guides blood from a digestive system to the liver. The hepatic artery branches off from a ventral aorta. The hepatic vein branches off from an inferior vena cava. However, types in the present embodiment may be those that minutely classify blood vessels. For example, a relatively thick hepatic artery and a thin hepatic artery may be classified as different types. Alternatively, in partial hepatectomy, the liver is classified as the right hepatic lobe, the left hepatic lobe, and the caudate lobe, and the right hepatic lobe and the left hepatic lobe are further classified into a plurality of sections. However, the blood vessel type in the present embodiment may be the one in consideration of to which section a blood vessel is connected. For example, in the present embodiment, a right hepatic vein, a middle hepatic vein, and a left hepatic vein may be classified as different types.

FIGS. 14A and 14B are diagrams each illustrating an example of the database in accordance with the present embodiment. In the creation process that creates the database that has been described with reference to FIG. 4, the bleeding pattern image sequence is associated with information indicating the blood vessel type of the blood vessel on which the bleeding has been occurring as illustrated in FIG. 14A. That is, in step S12 in FIG. 4, by performing annotation that adds the blood vessel type as the metadata, the database illustrated in FIG. 14A is acquired.

As illustrated in FIG. 14B, the database includes data that associates a blood vessel type and a bleeding stopping treatment in accordance with the blood vessel type with each other. For example, FIG. 14B is a table including data having the number of rows corresponding to target blood vessel types, and one blood vessel type is associated with one bleeding stopping treatment. Note that conceivable examples of bleeding stopping treatments include suturing of a blood vessel, burning and sealing of a blood vessel using an energy device, clipping performed by pinching of the vicinity of the bleeding point with a clip to mechanically perform compression, and injection or dispersion of a medicine exhibiting blood vessel contractive action. Note that the number of blood vessel types and the number of kinds of bleeding stopping treatment are not necessarily matched with each other, and one bleeding stopping treatment is not prevented from being associated with a plurality of blood vessel types.

The determination process that determines the bleeding stopping treatment in accordance with the present embodiment may be a process using machine learning. Specifically, the training device 500 performs machine learning based on the database to generate the trained model. The processing section 120 of the image processing system 100 operates in accordance with the trained model generated by the training device 500 to determine the bleeding stopping treatment. The following description will be given of machine learning using a neural network, but the method in accordance with the present embodiment is not limited thereto. In the present embodiment, for example, machine learning using another model such as a support vector machine (SVM) may be performed, and machine learning using a method that has developed from various methods such as the neural network and the SVM may be performed.

Figure 15A:
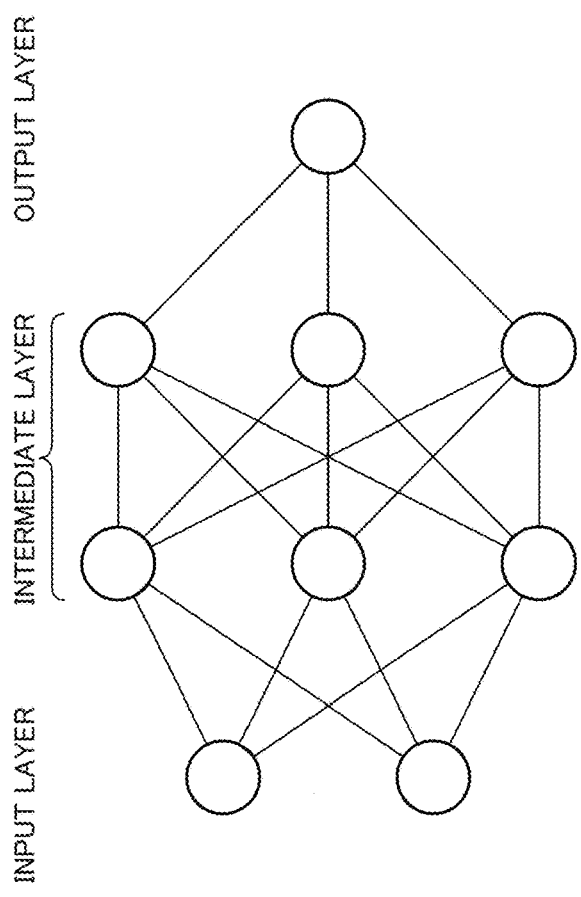
FIGS. 15A and 15B each illustrate an example of a neural network.

FIG. 15A is a schematic diagram for describing the neural network. The neural network includes an input layer that takes input data, an intermediate layer that executes calculation based on output from the input layer, and an output layer that outputs data based on output from the intermediate layer. While 15A exemplifies a network having the intermediate layer composed of two layers, the intermediate layer may be composed of one layer, or three or more layers. In addition, the number of nodes (neurons) included in each layer is not limited to that in the example of FIG. 15A, and can be modified in various manners. Note that in consideration of accuracy, it is preferable to use deep learning using a multi-layer neural network for training in accordance with the present embodiment. The multi-layer mentioned herein means four or more layers in a more limited sense.

As illustrated in FIG. 15A, a node included in a given layer is connected to a node in an adjacent layer. A weight coefficient is assigned between connected nodes. Each node multiplies output from a node in a former stage by the weight coefficient and obtains a total value of results of multiplication. Furthermore, each node adds a bias to the total value and applies an activation function to a result of addition to obtain output from the node. This process is sequentially executed from the input layer to the output layer, whereby output from the neural network is obtained. Note that as the activation function, various functions such as a sigmoid function and a rectified linear unit (ReLU) function are known, and a wide range of these functions can be applied in the present embodiment.

Training in the neural network is a process that determines an appropriate weight coefficient (including a bias). Specifically, the training device 500 inputs input data out of training data to the neural network and performs calculation in the forward direction using the weight coefficient at this time to obtain output. The training device 500 calculates an error function based on the output and a correct label out of the training data. The training device 500 then updates the weight coefficient to make the error function smaller. In updating the weight coefficient, for example, backpropagation that updates the weight coefficient from the output layer to the input layer can be utilized.

Figure 15B:

The neural network may be, for example, a convolutional neural network (CNN). FIG. 15B is a schematic diagram for describing the CNN. The CNN includes a convolution layer that performs convolution calculation and a pooling layer. The convolution layer is a layer that performs a filter process. The pooling layer is a layer that reduces a size in a vertical direction and a size in a lateral direction to perform pooling calculation. In the example illustrated in FIG. 15B, the CNN is a network that causes each of the convolution layer and the pooling layer to perform calculation multiple times, thereafter causes a fully connected layer to perform calculation, and thereby obtains output. The fully connected layer is a layer in which calculation is performed in a case where all nodes in the former layer are connected to nodes in a given layer, and corresponds to calculation in each layer described with reference to FIG. 15A. Note that the calculation process with the activating function is omitted in FIG. 15B. Various configurations of the CNN have been known, and a wide range of these configurations are applicable to the present embodiment.

In a case where the CNN is used, a procedure of processing is similar to that illustrated in FIG. 15A. That is, the training device 500 inputs input data, out of the training data, to the CNN, and performs a filter process or pooling calculation using filter characteristics at that time to obtain output. The training device 500 calculates the error function based on the output and the correct label, and updates the weight coefficient including the filter characteristics to make the error function smaller. For example, the backpropagation can be utilized also when the weight coefficient of the CNN is updated.

Figure 16:
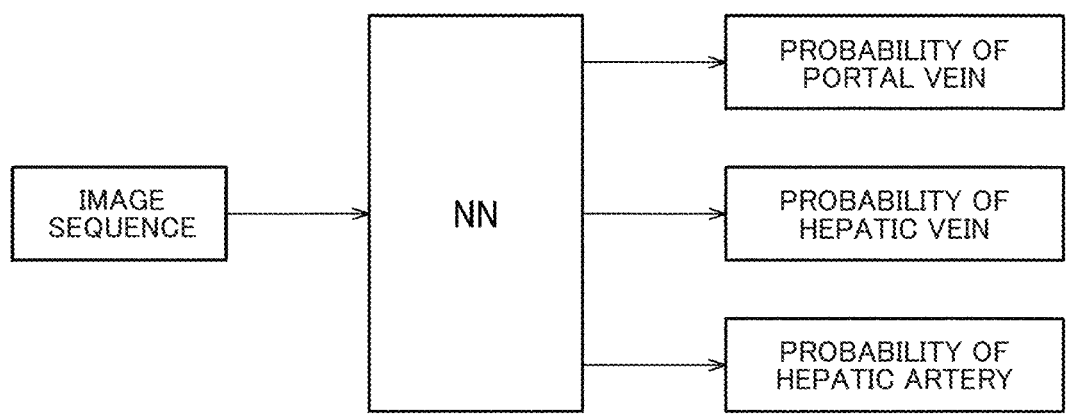
FIG. 16 illustrates an example of input to and output from the neural network.

FIG. 16 is a diagram that exemplifies input and output to/from the neural network in a case of using the database illustrated in FIG. 14A. As illustrated in FIG. 16, input data to the neural network is an image sequence, and output data is information for identifying a bleed vessel type. The image sequence serving as input has, for example, a fixed length, but is not prevented from having a variable length depending on a configuration of the neural network. In a case where the output layer of the neural network is a known softmax layer, the output data is probability data indicating a probability of each blood vessel type. In the example of FIG. 16, the output data is the following three pieces of data indicating a blood vessel type of a blood vessel on which a bleeding has been occurring. The first data is "probability data indicating a probability of the portal vein". The second data is "probability data indicating a probability of the hepatic artery". The third data is "probability data indicating a probability of the hepatic vein".

The training device 500 acquires the bleeding pattern image sequence and the blood vessel type information with which the image sequence is associated from the database illustrated in FIG. 14A. Subsequently, the training device 500 inputs the image sequence in the neural network and performs calculation in a forward direction using the weight coefficient at this time to obtain the three pieces of probability data. In a case where the blood vessel type information indicates "the portal vein", data in which the "probability data indicating a probability of the portal vein" is 1, and each of the "probability data indicating a probability of the hepatic artery" and the "probability data indicating a probability of the hepatic vein" is 0 is a correct answer. The training device 500 calculates, as the error function, an error between the three pieces of probability data obtained by calculation in the forward direction and the correct answer. The backpropagation or the like is used for the update process that updates the weight coefficient to make the error function smaller, as described above. This is the processing executed by data of one row included in the database in FIG. 14A. The training device 500 repeats this processing to generate the trained model. Various methods for the training process such as batch training and mini-batch training have been known, and a wide range of these methods are applicable to the present embodiment.

Figure 17:
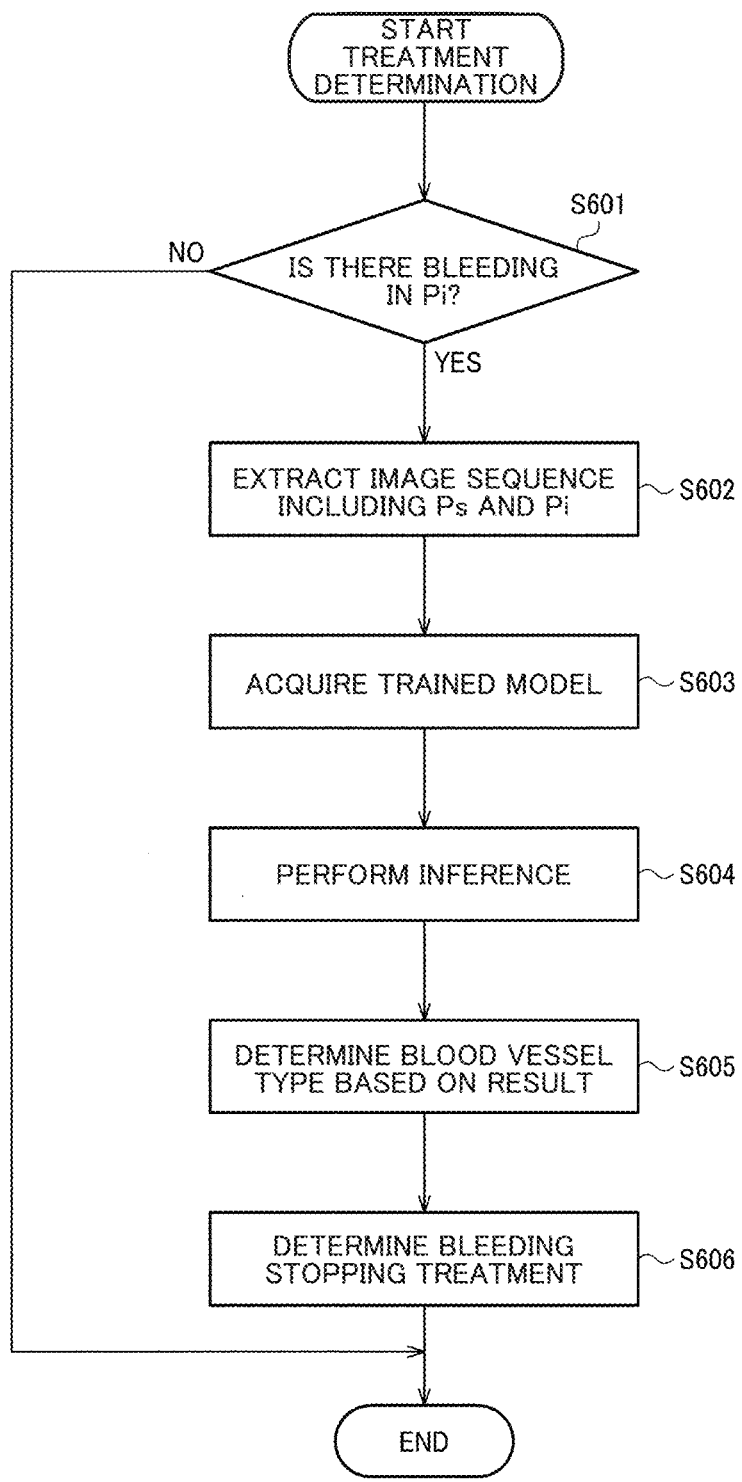
FIG. 17 is a flowchart describing a determination process that determines a bleeding stopping treatment.

FIG. 17 is a flowchart describing the determination process that determines the bleeding stopping treatment in step S203. Assume that the trained model has been generated by the above-mentioned processing before the processing in FIG. 17 is started.

First, in step S601, the treatment determination section 125 determines whether or not a bleeding has been occurring in the latest image Pi. For example, the treatment determination section 125 acquires a result of the process of the bleeding detection section 121 in step S201 to perform a process in step S601. In a case where no bleeding has been occurring, the treatment determination section 125 omits step S602 or subsequent steps, and ends the processing.

When determining that the bleeding has been occurring, in step S602, the treatment determination section 125 performs a process that extracts an image sequence to be input to the trained model from the processing target image sequence. The image sequence mentioned herein is images representing a bleeding state. A start point of the image sequence is, for example, the image Ps. An end point of the image sequence is, for example, the image Pi. However, a range of the image sequence to be extracted is not limited thereto, and at least one of the start point or the end point may be different. In addition, the range of the image sequence to be extracted is not limited to the one that includes images in all frames from the start point to the end point, and part of images in the middle may be omitted.

In step S603, the treatment determination section 125 acquires the trained model generated by the training device 500. The process in step S603 may be a process that receives the trained model from the database server 300. Alternatively, the treatment determination section 125 may preliminarily acquire the trained model from the database server 300, and store the trained model in the storage section 130. In this case, the process in step S603 corresponds to the process that reads out the stored trained model. Note that the order of the processes in steps S602 and S603 is not limited thereto, and the process in step S603 may be performed before the process in step S602, or the two processes may be performed in parallel.

In step S604, the treatment determination section 125 performs an inference process based on the trained model. Specifically, the treatment determination section 125 inputs the extracted image sequence to the trained model to acquire output data. A process in step S604 is, for example, calculation in the forward direction including the filter process corresponding to the convolution layer. The output data is, for example, the three pieces of probability data as described above with reference to FIG. 16.

In step S605, the treatment determination section 125 performs a process that identifies a blood vessel type on which the bleeding has been occurring based on the output data. The process in step S605 is, for example, a process that selects data having a maximum value out of the three pieces of probability data.

In step S606, the treatment determination section 125 determines a bleeding stopping treatment based on the identified blood vessel type. For example, the treatment determination section 125 performs a comparison process that compares the database illustrated in FIG. 14B and the blood vessel type identified in step S605 to determine the bleeding stopping treatment. In the example illustrated in FIG. 14B, in a case where the blood vessel type is identified as the portal vein, the bleeding stopping treatment is suturing.

As described above, the database in accordance with the present embodiment may include a plurality of datasets in each of which an in-vivo image sequence corresponding to in-vivo images captured in a time-series manner is associated with the blood vessel type information indicating a type of a blood vessel on which a bleeding whose image has been captured in the in-vivo image sequence. The database is, for example, as illustrated in FIG. 14A. The processing section 120 performs a process that identifies the blood vessel type of the blood vessel on which the bleeding has been occurring, based on the trained model and the processing target image sequence. The trained model is a trained model that has machine-learned a relationship between the in-vivo image sequence and the blood vessel type information based on the plurality of datasets described above. Furthermore, the processing section 120 determines a bleeding stopping treatment based on the identified type.

Identifying the blood vessel type using the trained model in this manner enables accurate estimation of the blood vessel type of the blood vessel on which the bleeding has been occurring, and also enables presentation of the bleeding stopping treatment in accordance with the blood vessel type to the user.

Note that calculation in accordance with the trained model in the processing section 120, that is, calculation for outputting output data based on input data may be executed by software, or hardware. In other words, product-sum calculation executed at each node in FIG. 15A, or a filter process executed in the convolution layer of the CNN may be executed by software. Alternatively, the above-mentioned calculation may be executed by a circuit device such as a FPGA circuit. Still alternatively, the above-mentioned calculation may be executed by software and hardware in combination. In this manner, operations of the processing section 120 in accordance with an instruction from the trained model stored in the storage section 130 can be implemented in various manners. For example, the trained model includes an inference algorithm, and a parameter used in the inference algorithm. The inference algorithm is an algorithm for performing product-sum calculation or the like based on the input data. The parameter is a parameter acquired by a training process, and is, for example, a weight coefficient. In this case, both the inference algorithm and the parameter are stored in the storage section 130, and the processing section 120 may read out the inference algorithm and the parameter and thereby perform the inference process with software. Alternatively, the inference algorithm may be implemented by the FPGA circuit or the like, and the storage section 130 may store the parameter.

3.3 Display Process

Figure 18:
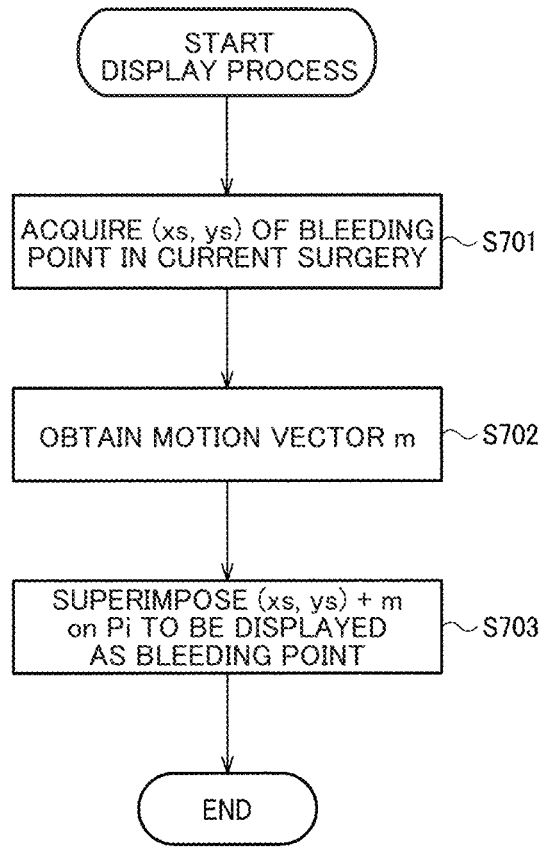
FIG. 18 is a flowchart describing a display process.

FIG. 18 is a flowchart describing the display process in step S103. First, in step S701, the display processing section 127 acquires the bleeding point (xs, ys) in the bleeding start image Ps of the bleeding point serving as a target in surgery being currently conducted. For example, the display processing section 127 reads out data illustrated in FIG. 13 to identify coordinates of the bleeding point in the image Ps.

In step S702, the display processing section 127 performs a correction process that corrects the bleeding point based on an amount of movement of the object between images. Note that the bleeding point detection section 123 may perform the correction process that corrects the bleeding point, and the display processing section 127 may acquire a result of the correction process.

For example, the display processing section 127 calculates the amount of movement of the object between the image Ps and the image Pi in the latest frame serving as a display target. The amount of movement mentioned herein is, for example, a motion vector. The motion vector can be obtained, for example, by block matching or the like. Performing the correction process based on the obtained motion vector on a position of the bleeding point in the image Ps enables identification of the position of the bleeding point in the image Pi. Note that the correction process that corrects the bleeding point is not limited to the correction process that is directly executed between the image Ps and the image Pi. For example, the display processing section 127 obtains a motion vector between the image Ps and an image Ps+1, and performs a process that identifies the bleeding point in the image Ps+1 based on the motion vector. From this process forward, the display processing section 127 may similarly correct the bleeding point one frame by one frame to identify the bleeding point in the image Pi. Note that the display processing section 127 may perform a process that identifies the bleeding point every two frames to correct the bleeding point, and the specific process can be modified in various manners.

In step S703, the display processing section 127 generates a display image based on a display target image and information of the bleeding point identified with respect to the image. Specifically, the display processing section 127 adds, to the image Pi, a result of correction on the bleeding point (xs, ys) in the bleeding start image Ps with the motion vector to perform display regarding the bleeding point. The display processing section 127, for example, performs a process that superimposes a marker object that clearly indicates the position of the bleeding point on the display target image.

Figure 19:
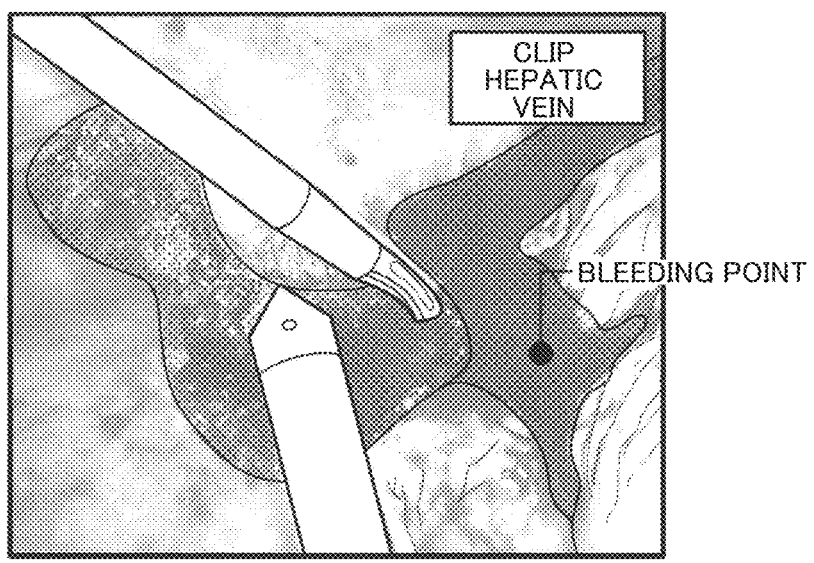
FIG. 19 illustrates an example of a display image for presenting the bleeding stopping treatment.

FIG. 19 illustrates an example of the display image for presenting the determined bleeding stopping treatment to the user. As illustrated in FIG. 19, the display image is, for example, an image in which information indicating the bleeding stopping treatment is superimposed on an image captured with the inside of the living body. In FIG. 19, by superimposing a text of "clipping", recommendation of clipping as the bleeding stopping treatment is presented. However, superimposed information is not limited to a text, and may be an image or an icon. Alternatively, a presentation process that presents the bleeding stopping treatment may be performed using a method other than a display method. For example, the processing section 120 may use audio or the like to present the bleeding stopping treatment to the user.

Additionally, as illustrated in FIG. 19, information indicating the bleeding point or information indicating the blood vessel type of the blood vessel on which the bleeding has been occurring may be superimposed on the display image. Displaying such additional information enables presentation in a mode in which the user easily understands the bleeding state. For example, displaying the bleeding point allows the user to grasp a position at which the bleeding stopping treatment should be performed.

In this manner, the processing section 120 may perform a bleeding notification process that notifies the user of the information regarding the bleeding point identified by the bleeding point detection process. Presenting the bleeding point to the user can facilitate the bleeding stopping treatment performed by the user. While the example of displaying the bleeding point is described in FIG. 18, the bleeding notification process may include a process that makes notification of information regarding occurrence of the bleeding when it is determined that the bleeding has been occurring in the bleeding point detection process. Alternatively, the bleeding notification process may be a process that makes notification of both the information regarding occurrence of the bleeding and the information regarding the bleeding point.

3.4 Update Process that Updates Database

Additionally, the processing section 120 performs a process that adds, to the database, the dataset in which the processing target image sequence used for determination of the bleeding stopping treatment and the bleeding stopping treatment for the bleeding detected in the processing target image sequence are associated with each other. With this process, data stored in the database is expanded with execution of surgery. This enables an increase in accuracy of processing using the database. When machine learning is used, an increase in amount of training data enables generation of the trained model capable of executing an inference process with high accuracy.

The flow of the update process that updates the database is pursuant to the creation process that creates the database illustrated in FIG. 4. Since the process that extracts the image sequence is performed in step S602 of the determination process that determines the bleeding stopping treatment, a result of the process in step S602 can be used for the process in step S11. For example, the image sequence stored in the database is the image sequence in which the image Ps is the start point and the image Pi is the end point. However, the user is not prevented from redoing the process that extracts the image sequence such as adjustment of the range of the image sequence.

In step S606 of the determination process that determines the bleeding stopping treatment, the bleeding stopping treatment has been determined. If bleeding stopping has been completed properly by the bleeding stopping treatment, the metadata to be added in the process in step S12 is information indicating the bleeding stopping treatment that has been actually executed. In a case where a bleeding stopping effect provided by the executed bleeding stopping treatment is insufficient, a process that associates the image sequence with information indicating the insufficiency, information indicating another bleeding stopping treatment that is determined as preferable by a skilled doctor, or other information.

Association of the additional information in step S13 and the registration process to the database in step S14 are similar to those in the example in FIG. 4.

4. Modification

Some modifications will be described below.

4.1 Modification in Partial Hepatectomy

As described above, the processing target image sequence and the in-vivo images included in the database may be images captured with the liver. Specifically, surgery assumed in the present embodiment may be surgery on the liver, and partial hepatectomy in a more limited sense.

In partial hepatectomy, a method called a Pringle method is used. This is a method of stopping the hepatic artery and the portal vein with clamp forceps to interrupt the bloodstream. Usage of the Pringle method enables suppression of a bleeding during surgery. A large-scale bleeding that has been occurring during a Pringle maneuver has a greater probability of being a bleeding from the hepatic vein. In a case where a bleeding has been occurring after the Pringle maneuver is released, the bleeding has a greater probability of being a bleeding from the portal vein or the hepatic artery.

Hence, the processing section 120 identifies whether or not the Pringle maneuver that interrupts the bloodstream of the hepatic artery and the portal vein has been performed, and performs the determination process that determines the bleeding stopping treatment based on a result of the identification. This enables determination in consideration of whether the Pringle maneuver is being performed or has been released, and thereby enables execution of the determination process that determines the bleeding stopping treatment with high accuracy.

For example, the user may perform input indicating whether the Pringle maneuver is being performed or has been released. The processing section 120 identifies whether or not the Pringle maneuver is being performed based on the input from the user. However, the processing section 120 may identify whether or not the Pringle maneuver is being performed based on an image process.

For example, the database may include two tables of a first table and a second table. In the first table, an image sequence captured when the bleeding has been occurring during the Pringle maneuver is associated with the blood vessel type information. In the second table, an image sequence captured when the bleeding has been occurring after release of the Pringle maneuver is associated with the blood vessel type information. The training device 500 generates a first trained model based on the first table, and generates a second trained model based on the second table.

The processing section 120 identifies whether or not the Pringle maneuver that interrupts the bloodstream of the hepatic artery and the portal vein has been performed. When identifying that Pringle maneuver is being performed, the processing section 120 determines a bleeding stopping treatment based on the first trained model. When identifying that Pringle maneuver has been released, the processing section 120 determines a bleeding stopping treatment based on the second trained model. This enables output of a treatment result depending on the Pringle maneuver.

Alternatively, the processing section 120 may determine, based on the processing target image sequence and the database, a first bleeding stopping treatment performed when the Pringle maneuver is being performed and a second bleeding stopping treatment performed when the Pringle maneuver is not being performed. For example, the display processing section 127 displays both of the two bleeding stopping treatments. For example, the display processing section 127 displays two pieces of information such as "during Pringle maneuver: suturing" and "after release of Pringle maneuver: clipping" side by side. The user during surgery grasps the Pringle maneuver is now being performed or has been released. Hence, even when the two pieces of information are presented, the user can easily understand to which information to be referred.

Figures 20A, 20B:
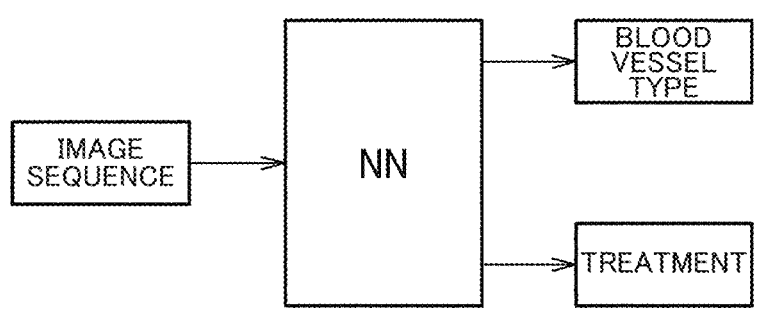
FIG. 20A illustrates another example of the database.
FIG. 20B illustrates another example of input to and output from the neural network.

For example, the processing section 120 inputs the processing target image sequence to both the first trained model and the second trained model. The processing section 120 determines the first bleeding stopping treatment based output from the first trained model, and determines the second bleeding stopping treatment based output from the second trained model 4.2 Modification of Machine Learning FIG. 20A is a diagram for describing another configuration of the database. As illustrated in FIG. 20A, the bleeding pattern image sequence is associated with the blood vessel type information indicating the blood vessel type of the blood vessel on which the bleeding has been occurring and information indicating a recommended bleeding stopping treatment. Specifically, in step S12 in FIG. 4, by performing annotation that adds the blood vessel type and the bleeding stopping treatment as the metadata, the database illustrated in FIG. 2oA is acquired.

FIG. 20B is a diagram that exemplifies input and output to/from the neural network when the database illustrated in FIG. 20A is used. As illustrated in FIG. 20B, input data to the neural network is the image sequence, and output data is information for identifying the blood vessel type and information for identifying the bleeding stopping treatment. The information for identifying the blood vessel type is, for example, probability data indicating a probability of each blood vessel type similarly to the example in FIG. 16. The information for identifying the bleeding stopping treatment is, for example, probability data indicating a probability of recommendation of each bleeding stopping treatment. The information for identifying the bleeding stopping treatment includes, for example, "probability data for recommending suturing", "probability data for recommending clipping", and "probability data for recommending burning and sealing".

The training device 500 performs machine learning with the image sequence among FIG. 20A serving as input and the information indicating the blood vessel type and the recommended bleeding stopping treatment in FIG. 20A serving as a correct label to generate the trained model. The treatment determination section 125 of the image processing system 100 inputs the processing target image sequence to the trained model. In a case where the neural network illustrated in FIG. 20B is used, it is possible to determine both the blood vessel type and the bleeding stopping treatment as output from the trained model.

The identification of the blood vessel type and the determination of the bleeding stopping treatment are not limited to those performed in a stepwise manner, and may be performed in parallel as illustrated in FIG. 20B. Also in this case, it is possible to present a blood vessel type and a bleeding stopping treatment appropriate for the bleeding stopping treatment to the user. Note that as illustrated in FIG. 20A, in the database mentioned herein, an identical blood vessel type may be associated with different bleeding stopping treatments. For this reason, it is possible to flexibly change a bleeding stopping treatment with respect to the identical blood vessel depending on situations.

Figure 21A:
FIG. 21A illustrates another example of the database.

Note that the method in accordance with the present embodiment is to present the recommended bleeding stopping treatment to the user. Thus, determination and presentation of the blood vessel type is not necessarily performed. FIG. 21A is a diagram for describing another configuration of the database. As illustrated in FIG. 21A, the bleeding pattern image sequence may be associated with information indicating the recommended bleeding stopping treatment.

Figure 21B:
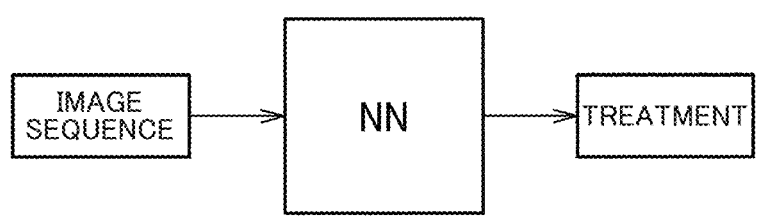
FIG. 21B illustrates another example of input to and output from the neural network.

FIG. 21B is a diagram that exemplifies input and output to/from the neural network when the database illustrated in FIG. 21A is used. As illustrated in FIG. 21B, input data to the neural network is the image sequence, and output data is information for identifying the bleeding stopping treatment. In this manner, even in a case where the blood vessel type is omitted, it is possible to determine and present the recommended bleeding stopping treatment.

As described above with reference to FIGS. 20A and 21A, the database may include a plurality of datasets in each of which the in-vivo image sequence corresponding to in-vivo images captured in a time-series manner is associated with the bleeding stopping treatment information indicating the recommended bleeding stopping treatment for the bleeding whose image has been captured in the in-vivo image sequence. The processing section 120 performs the process that determines the bleeding stopping treatment based on the processing target image sequence and the trained model that has machine-learned a relationship between the in-vivo image sequence and the bleeding stopping treatment information based on the plurality of datasets. This enables acquisition of information indicating the bleeding stopping treatment as output from the trained model.

While the above description has been given of the example in which input to the trained model is the image sequence, the method in accordance with the present embodiment is not limited thereto. For example, a feature amount obtained based on each image included in the image sequence may be used as input to the trained model. The feature amount may be information regarding a hue, saturation, brightness, or the like. Alternatively, the feature amount may be information indicating a change of bleeding speed in time series. The bleeding speed represents a bleeding amount per unit time. As described above, an image of a region in which blood exits is captured as the red region. Although it is difficult to estimate an absolute bleeding amount with high accuracy, the area of the red region is information serving as an index for a bleeding amount. Hence, a change in area of the red region can be utilized as the index for the bleeding speed. By using the bleeding speed itself, intensity of the bleeding can be determined. By seeing a degree of change in bleeding speed, presence/absence of pulsation can be determined. For example, the feature amount indicating a bleeding situation is a waveform indicating a time change in bleeding speed. However, the feature amount may be an amount of statistics such as an average value, a mean value, or the like of the bleeding speed, may be an amount of statistics of a change in bleeding speed, or may be a combination thereof. The specific mode can be modified in various manners.

Note that the output data obtained by inputting of the feature amount to the neural network may be the blood vessel type, the bleeding stopping treatment, or both thereof as described above.

Figure 22:
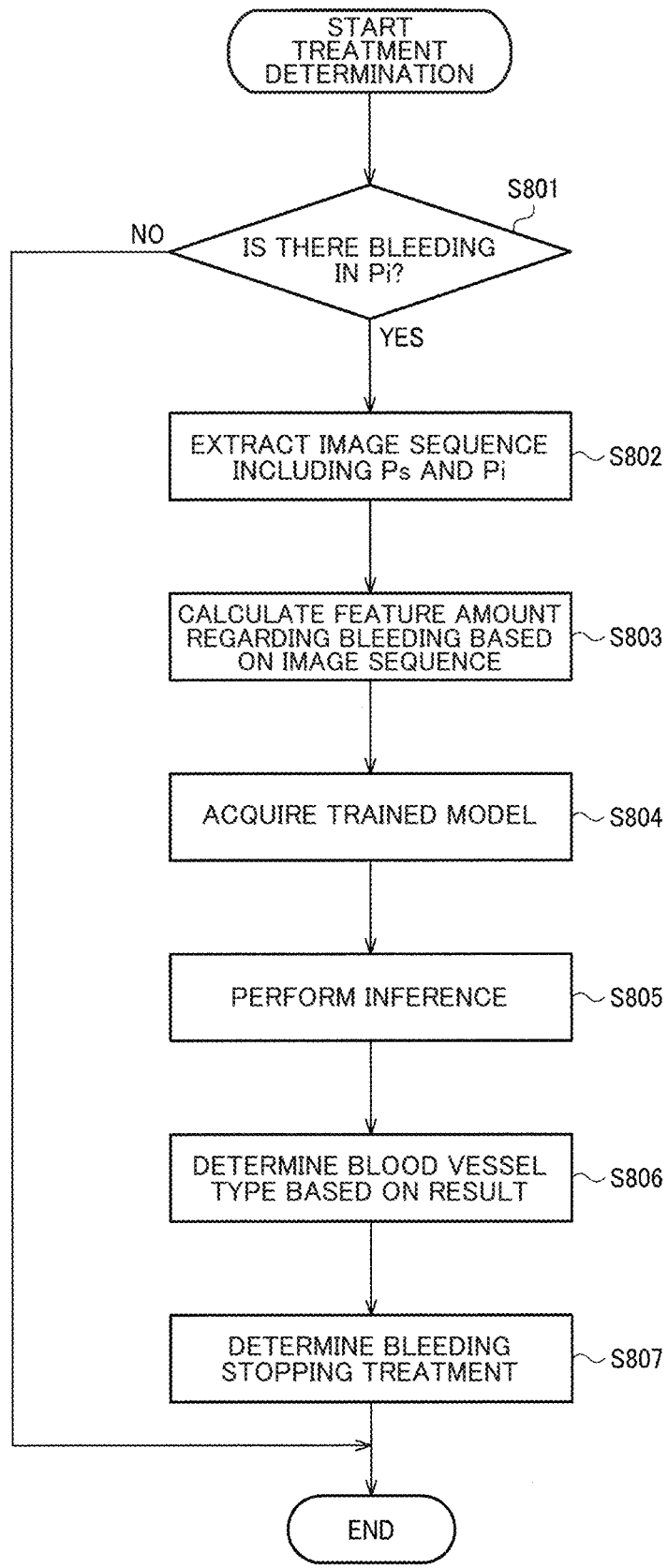
FIG. 22 is a flowchart describing the determination process that determines the bleeding stopping treatment.

FIG. 22 is a flowchart describing the determination process that determines the bleeding stopping treatment in a case where the feature amount serves as input data. Steps S801 and S802 in FIG. 22 are similar to steps S601 and S602 in FIG. 17, respectively. Subsequently, in step S803, the treatment determination section 125 calculates a feature amount based on the extracted image sequence. For example, the treatment determination section 125 obtains the feature amount corresponding to bleeding speed based on a time change of the red region in the image.

In step S804, the treatment determination section 125 acquires the trained model generated by the training device 500. In step S805, the treatment determination section 125 executes an inference process based on the trained model. Specifically, the treatment determination section 125 inputs the calculated feature amount to the trained model to acquire output data. Since the processes in steps S806 and S807 are similar to the processes in steps S605 and S606 in FIG. 17, respectively.

4.3 Modification of Processing Based on Database

The above description has been given of the example in which the determination process that determines the bleeding stopping treatment based on the database is the process using machine learning. However, the method in accordance with the present embodiment is not limited to the machine learning.

The processing section 120 may compare the in-vivo image sequence included in the database and the processing target image sequence to perform the determination process that determines the bleeding stopping treatment. For the comparison between images, known is a method of obtaining a histogram for each of a hue, saturation, and brightness from the images and comparing histograms. Since each of the in-vivo image sequence and the processing target image sequence has a plurality of images, the processing section 120, for example, repeats a comparison process that compares two images multiple times to calculate a degree of similarity between the images.

The processing section 120 determines an image sequence that is the most similar to the processing target image sequence among a plurality of in-vivo image sequences included in the database. In a case where the database illustrated in FIG. 14A is used, the processing section 120 determines that a bleeding has been occurring in a blood vessel type with which the determined in-vivo image sequence is associated. A process after determination of the blood vessel type is similar to that in the above-mentioned example. The same applies to a case of the database illustrated in FIG. 20A or FIG. 21A, and identifying the in-vivo image sequence that is similar to the processing target image sequence enables determination of both the blood vessel type and the bleeding stopping treatment or determination of the bleeding stopping treatment.

In a case of comparing the database and the processing target image sequence, the feature amount such as the above-mentioned histogram may be calculated every time comparison is made. However, when the creation process that creates the database is performed, the feature amount may be calculated from the in-vivo image sequence, and the database in which the feature amount, the blood vessel type, the bleeding stopping treatment, and the like are associated with one another may be created. For example, the database creation device 400 creates a database in which the feature amount such as the histogram is associated with the blood vessel type information, instead of the database illustrated in FIG. 14A, and transmits the database to the database server 300.

Note that the comparison between the in-vivo image sequence and the processing target image sequence is a process that searches for an image sequence that is similar in a bleeding state. Hence, as the feature amount used for comparison, a feature amount indicating the bleeding in an image may be used. The feature amount indicating the bleeding is a bleeding amount, bleeding speed, a time change in bleeding speed, or the like.

FIG. 23A is a diagram for describing another configuration of the database. As illustrated in FIG. 23A, a waveform indicating a time change in bleeding speed is associated with information indicating the blood vessel type of the blood vessel on which the bleeding has been occurring. For example, the database creation device 400 obtains the area of the red region from each image of the in-vivo image sequence, and performs a process that obtains the waveform indicating the time change in bleeding speed based on differential information. The differential information is a difference between two images that are adjacent to each other.

The treatment determination section 125 performs, on the processing target image sequence, a process that obtains the area of the red region and a process that obtains differential information to obtain the waveform indicating the time change in bleeding speed in the processing target image sequence. Subsequently, the treatment determination section 125 calculates a similarity between waveforms each indicating the time change in bleeding speed. The treatment determination section 125 then determines that the bleeding has been occurring in the blood vessel type associated with a waveform indicating the time change in bleeding speed and having the highest similarity. Processing after determination of the blood vessel type is similar to that in the above-mentioned example. As illustrated in FIG. 23B, the database includes data that associates a blood vessel type and a bleeding stopping treatment in accordance with the blood vessel type with each other. FIG. 23B is similar to FIG. 14B. The treatment determination section 125 determines a bleeding stopping treatment based on the comparison process that compares the blood vessel type determined based on FIG. 23A and the table illustrated in FIG. 23B.

4.4 Emergency Bleeding Stopping Treatment

The above description has been given of the example in which, when the bleeding is detected in the image Pi in the latest frame, the bleeding stopping treatment is determined based on the image sequence with the bleeding start image Ps serving as the start point and the image Pi serving as the end point. However, the bleeding stopping treatment may be determined based on execution/non-execution of an emergency bleeding stopping treatment by the user.

For example, the treatment determination section 125 determines, instead of the process in step S601 in FIG. 17 or the process in step S801 in FIG. 22, whether or not the display process regarding the bleeding point has been executed in past frames, and whether or not the emergency bleeding stopping treatment has been executed by the user.

With the display process that displays the bleeding point in step S103 in FIG. 7, it is possible to prompt the user to execute the emergency bleeding stopping treatment for the bleeding. The emergency bleeding stopping treatment represents a treatment that is more emergent than the bleeding stopping treatment that is determined by the determination process that determines the bleeding stopping treatment in accordance with the present embodiment. The emergency bleeding stopping treatment is, specifically, astriction using a cover of a treatment tool, gauze inserted into an abdominal cavity, or the like. This is a treatment that inhibits the bloodstream by compression to suppress a bleeding, and is less effective in stopping the bleeding than clipping, burning and sealing, suturing, and the like that are presented as the bleeding stopping treatment. Since the emergency bleeding stopping treatment suppresses a severe bleeding an facilitates a treatment that is effective in stopping the bleeding such as clipping, it is effective to present the bleeding point first to prompt the emergency bleeding stopping treatment.

When determining that the emergency bleeding stopping treatment has been executed, the treatment determination section 125 executes the processes in step S602 and subsequent steps, or the processes in step S802 and subsequent steps. The determination of whether or not the emergency bleeding stopping treatment has been executed is performed based on, for example, input from the user. For example, the display screen displayed in step S103 or a manual of the endoscope system 200 may prompt the user to perform a predetermined input operation when the emergency bleeding stopping treatment has been completed. Alternatively, the determination of whether or not the emergency bleeding stopping treatment has been executed may be performed by an image process. Since the bleeding is temporarily suppressed by the emergency bleeding stopping treatment, the processing section 120 determines that the emergency bleeding stopping treatment has been executed, for example, in a case where the area of the red region becomes sufficiently small as compared to a timing at which it is determined that the bleeding has been occurring.

In this manner, when determining that the emergency bleeding stopping treatment for the bleeding has been executed by the user, the processing section 120 may perform a process that determines a treatment that exhibits higher bleeding stopping capability than that of the emergency bleeding stopping treatment as the bleeding stopping treatment, based on the processing target image sequence and the database.

The bleeding is suppressed by the emergency bleeding stopping treatment. At this time, a bleeding stopping effect provided by the emergency bleeding stopping treatment changes in accordance with a type of a damaged bleed vessel or a degree of damage. Performing the determination process that determines the bleeding stopping treatment after execution of the emergency bleeding stopping treatment enables determination of the bleeding stopping treatment in consideration of not only a state where the bleeding spreads, but also a state where the bleeding subsides due to the emergency bleeding stopping treatment. This can increase accuracy in estimating the bleeding stopping treatment. In accordance with circumstances, the bleeding has been sufficiently stopped by the emergency bleeding stopping treatment, and it is possible to determine that an additional bleeding stopping treatment is not necessary.

Note that as a conceivable use case for the endoscope system 200, as described in step S103 in FIG. 7, the processing section 120 first performs the bleeding notification process, and the user performs the emergency bleeding stopping treatment based on the bleeding notification process. Hence, the processing section 120 may perform the determination process that determines the bleeding stopping treatment based on the processing target image sequence and the database after execution of the bleeding notification process and execution of the emergency bleeding stopping treatment. However, the bleeding notification process is not essential and can be omitted in the present embodiment.

More specifically, the processing section 120 may perform the determination process that determines the bleeding stopping treatment based on the processing target image sequence including at least images captured during or after execution of the emergency bleeding stopping treatment by the user.

With this process, the images captured with a state where the bleeding is suppressed by the emergency bleeding stopping treatment are used for the determination process that determines the bleeding stopping treatment. This can increase processing accuracy in comparison with a case of considering only a state where a bleeding amount increases from the start of the bleeding. In the above-mentioned example, accuracy in the process that estimates the blood vessel type based on the processing target image sequence increases.

Note that as behaviors of the living body and the user, a bleeding occurs in the living body first, and then the user recognizes the bleeding. The recognition of the bleeding by the user may be performed by the bleeding notification process or may be voluntarily performed by the user's observation of an in-vivo image. The user then performs the emergency bleeding stopping treatment for the bleeding, and consequently, the bleeding is suppressed. As described above, the processing section 120 determines that the emergency bleeding stopping treatment has been executed based on, for example, a degree of reduction of the red region. In this case, at a timing when the processing section 120 determines that the emergency bleeding stopping treatment has been executed, whether the emergency bleeding stopping treatment continues to be executed or has been executed is unclear, but at least the bleeding is in a decreased state. Hence, by regarding the timing at which the processing section 120 determines that the emergency bleeding stopping treatment has been executed or subsequent timings as the end point of the processing target image sequence, it is possible to determine the bleeding stopping treatment in consideration of the state where the bleeding subsides. In a case where whether the emergency bleeding stopping treatment has been executed is determined based on input from the user, the user is only required to be prompted to perform input, for example, after the start of execution of the emergency bleeding stopping treatment. Also in this case, it becomes possible to determine the bleeding stopping treatment in consideration of the state where the bleeding subsides. In other words, by regarding the timing at which the processing section 120 determines that the emergency bleeding stopping treatment has been executed or subsequent timings as the end point of the processing target image sequence, it is possible to acquire the processing target image sequence including at least images captured during or after execution of the emergency bleeding stopping treatment by the user.

The start point of the processing target image sequence may be, as described above, for example, a timing corresponding to Ps described in FIG. 11, or a timing at which the bleeding has been occurring in the bleeding detection process described in FIG. 9. In a case where the processing section 120 performs the bleeding notification process, a timing of the start of the bleeding notification process may serve as the start point. Note that all images from the start point to the end point are not necessarily used for the determination process that determines the bleeding stopping treatment, and part of the images may be omitted. In a case where the image sequence input to the CNN has a fixed length, a thinning-out process or the like to adjust the length of the image sequence may be performed.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An image processing system, comprising:
at least one processor including hardware, wherein the processor being configured to perform
 a process that acquires, as a processing target image sequence, images captured in a time series manner with an inside of a living body by an endoscope imaging device, and
 a process based on the processing target image sequence and a database generated by using a plurality of in-vivo images captured at earlier timings than timings at which the processing target image sequence is captured, and
 a process that determines, when a bleeding has been occurring inside the living body, a kind of a bleeding stopping treatment desirable for a blood vessel on which the bleeding has been occurring based on the processing target image sequence and the database to present, to a user, the determined type of the bleeding stopping treatment.

2. The image processing system as defined in claim 1, wherein
the processor
 identifies a type of the blood vessel on which the bleeding has been occurring, based on the processing target image sequence and the database, and
 determines the kind of the bleeding stopping treatment based on the identified type.

3. The image processing system as defined in claim 2, wherein
the database includes a plurality of datasets in each of which an in-vivo image sequence representing the in-vivo images captured in a time series manner is associated with blood vessel type information, the blood vessel type information indicating the type of the blood vessel on which the bleeding being occurring is captured in the in-vivo image sequence, and
the processor
 performs a process that identifies the type of the blood vessel on which the bleeding has been occurring based on the processing target image sequence and a trained model, the trained model having machine-learned a relationship between the in-vivo image sequence and the blood vessel type information based on the plurality of datasets, and
 determines the kind of the bleeding stopping treatment based on the identified type.

4. The image processing system as defined in claim 1, wherein
the database includes a plurality of datasets in which an in-vivo image sequence representing the in-vivo images captured in a time series manner is associated with bleeding stopping treatment information, the bleeding stopping treatment information indicating a recommended kind of the bleeding stopping treatment for the bleeding captured in the in-vivo image sequence, and
the processor
 performs a process that determines the kind of the bleeding stopping treatment based on the processing target image sequence and a trained model, the trained model having machine-learned a relationship between the in-vivo image sequence and the bleeding stopping treatment information based on the plurality of datasets.

5. The image processing system as defined in claim 1, wherein
the processor performs a process that adds, to the database, a dataset in which the processing target image sequence used for determination of the bleeding stopping treatment and the kind of the bleeding stopping treatment for the bleeding detected in the processing target image sequence are associated with each other.

6. The image processing system as defined in claim 1, wherein
the processor
 performs a bleeding detection process that detects whether or not the bleeding has been occurring inside the living body based on the processing target image sequence, and
 performs, when the bleeding is detected, a bleeding point detection process that identifies a bleeding point serving as an occurrence position of the bleeding.

7. The image processing system as defined in claim 6, wherein
the processor performs a bleeding notification process that notifies the user of information regarding at least one of occurrence of the bleeding detected by the bleeding detection process or the bleeding point identified by the bleeding point detection process.

8. The image processing system as defined in claim 1, wherein
the processor performs, when determining that the user has executed an emergency bleeding stopping treatment for the bleeding, a process that determines a treatment that has higher bleeding stopping capability than a kind of the emergency bleeding stopping treatment as the kind of the bleeding stopping treatment, based on the processing target image sequence and the database.

9. The image processing system as defined in claim 8, wherein
the processor performs the process that determines the kind of the bleeding stopping treatment based on the processing target image sequence including images captured during execution of the emergency bleeding stopping treatment by the user or after the execution of the emergency bleeding stopping treatment.

10. The image processing system as defined in claim 1, wherein
the processing target image sequence and the in-vivo images are images captured with a liver,
the processor performs the process that determines the kind of the bleeding stopping treatment for a blood vessel that is any one of a hepatic artery, a hepatic vein, and a portal vein, based on the processing target image sequence and the database.

11. The image processing system as defined in claim 10, wherein
the processor performs a process that identifies whether or not a Pringle maneuver that interrupts bloodstream of the hepatic artery and the portal vein is being performed to determine the kind of the bleeding stopping treatment based on a result of the identification.

12. The image processing system as defined in claim 10, wherein
the processor determines, based on the processing target image sequence and the database, a kind of a first bleeding stopping treatment when a Pringle maneuver that interrupts bloodstream of the hepatic artery and the portal vein is being performed and a kind of a second bleeding stopping treatment when the Pringle maneuver is not being performed.

13. An endoscope system, comprising:
an imaging device that captures images of an inside of a living body; and
at least one processor including hardware,
wherein
the processor being configured to perform
a process that acquires, as a processing target image sequence, the images captured in a time series manner by the imaging device,
a process based on the processing target image sequence and a database generated by using a plurality of in-vivo images captured at earlier timings than timings at which the processing target image sequence is captured, and
a process that determines, when a bleeding has been occurring inside the living body, a kind of a bleeding stopping treatment desirable for a blood vessel on which the bleeding has been occurring based on the processing target image sequence and the database to present, to a user, the determined type of the bleeding stopping treatment.

14. An image processing method, comprising:
performing a process that acquires, as a processing target image sequence, images captured in a time series manner with an inside of a living body by an endoscope imaging device;
performing a process that determines, when a bleeding has been occurring inside the living body, a kind of a bleeding stopping treatment desirable for a blood vessel on which the bleeding has been occurring based on the processing target image sequence and a database generated by using a plurality of in-vivo images captured at earlier timings than timings at which the processing target image sequence is captured; and
performing a process that presents, to a user, the determined type of the bleeding stopping treatment.

* * * * *